United States Patent
Turchi et al.

(10) Patent No.: US 9,250,161 B2
(45) Date of Patent: Feb. 2, 2016

(54) TOOL FOR SAMPLING PLANT MATERIAL, AUTOMATION COMPRISING SAME, SAMPLING CELL PROVIDED WITH SUCH AN AUTOMATION AND SAMPLING METHOD

(71) Applicant: VILMORIN & CIE, Paris (FR)

(72) Inventors: Herve Turchi, Clapiers (FR); Guillaume Champain, Mauguio (FR); Remi Sayag, Saint Bauzille de Montmel (FR); Marc Havard, Ledenon (FR); Pierre Amouroux, Clermont Ferrand (FR)

(73) Assignee: VILMORIN & CIE, Paris (FR)

( * ) Notice: Subject to any disclaimer, the term of this patent is extended or adjusted under 35 U.S.C. 154(b) by 0 days.

(21) Appl. No.: 14/432,478

(22) PCT Filed: Oct. 7, 2013

(86) PCT No.: PCT/FR2013/052373
§ 371 (c)(1),
(2) Date: Mar. 30, 2015

(87) PCT Pub. No.: WO2014/053792
PCT Pub. Date: Apr. 10, 2014

(65) Prior Publication Data
US 2015/0260615 A1    Sep. 17, 2015

(30) Foreign Application Priority Data
Oct. 5, 2012    (FR) ...................................... 12 59526

(51) Int. Cl.
*A61B 10/00* (2006.01)
*G01N 1/08* (2006.01)
*G01N 1/04* (2006.01)
*G01N 1/28* (2006.01)

(52) U.S. Cl.
CPC .. *G01N 1/08* (2013.01); *G01N 1/04* (2013.01); *G01N 2001/2873* (2013.01)

(58) Field of Classification Search
CPC .................................. A61B 10/00; G01N 1/08
See application file for complete search history.

(56) References Cited

U.S. PATENT DOCUMENTS

| 3,921,459 | A | 11/1975 | Willett |
| 6,659,338 | B1 | 12/2003 | Dittmann et al. |
| 2008/0227662 | A1 | 9/2008 | Stromberg et al. |
| 2009/0139353 | A1 | 6/2009 | Kline et al. |

FOREIGN PATENT DOCUMENTS

WO    2004/063720 A1    7/2004

*Primary Examiner* — Jyoti Nagpaul
(74) *Attorney, Agent, or Firm* — Im IP Law PLLC; C. Andrew Im

(57) ABSTRACT

A sampling tool includes a guiding body provided with a through bore, and a part-carrying punch mounted slidingly adjustable in the bore having a lower edge forming a cutting edge. A part-carrying die of the tool is provided with a cutting upper edge and separated from the guiding body by an opening provided with a through bore which the lower end of the punch enters when cutting the sample to be collected. An actuator to actuate the punch between an initial position, a stationary intermediate position, and a final position in which the punch passes through the die. The path of the punch is tangential to the surface of the opening and the bore is tangential to a geometric plane containing the surface to make a cut with an open contour in the plant from which the sample is collected.

20 Claims, 20 Drawing Sheets

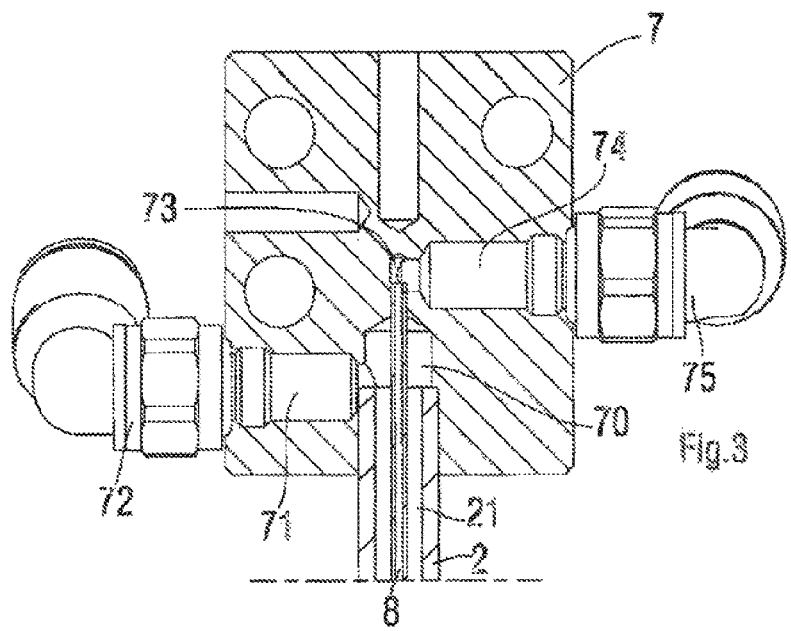
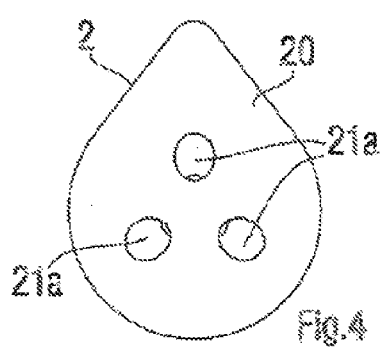
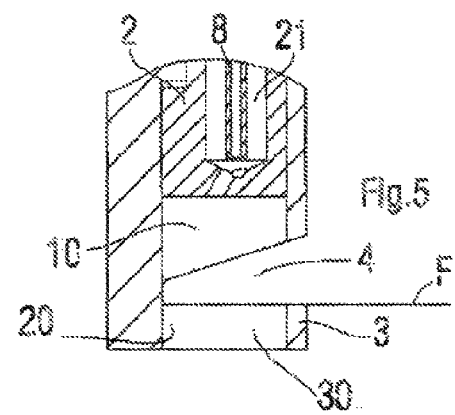
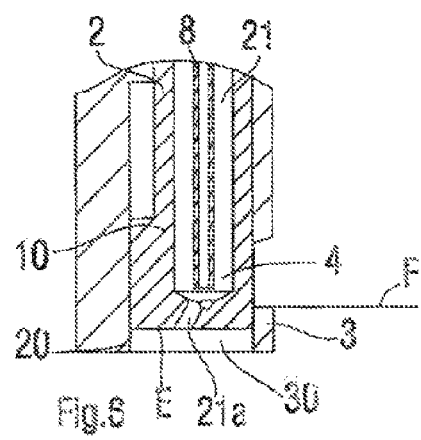
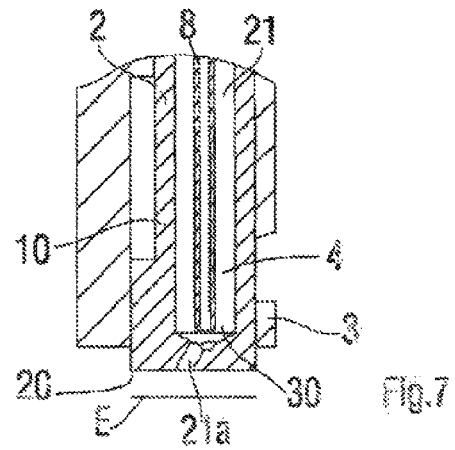

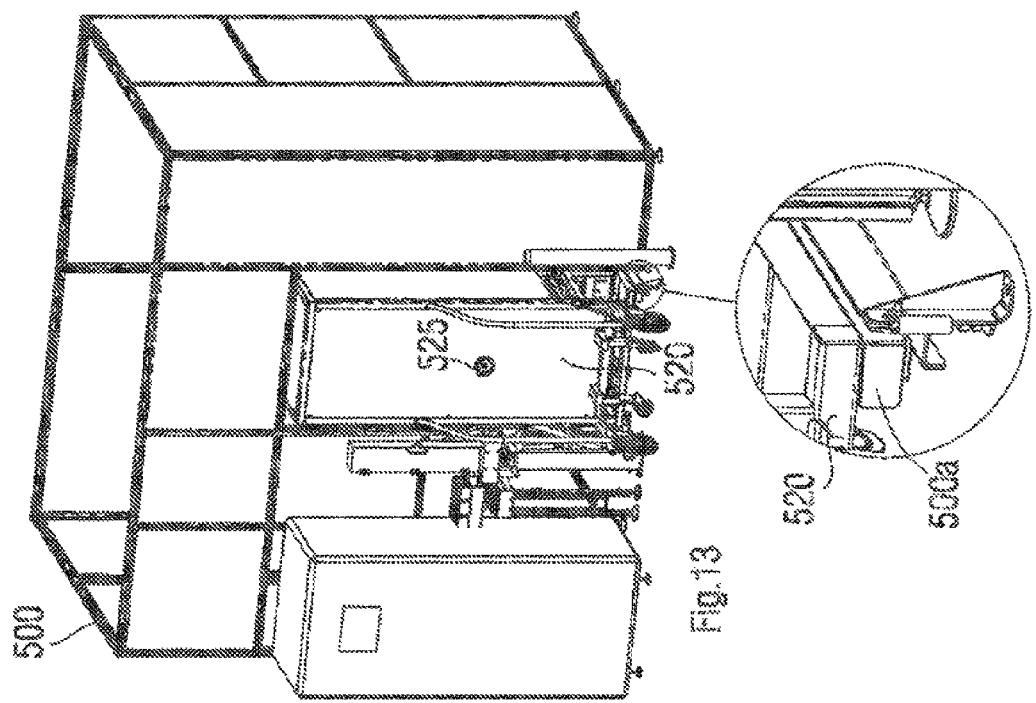

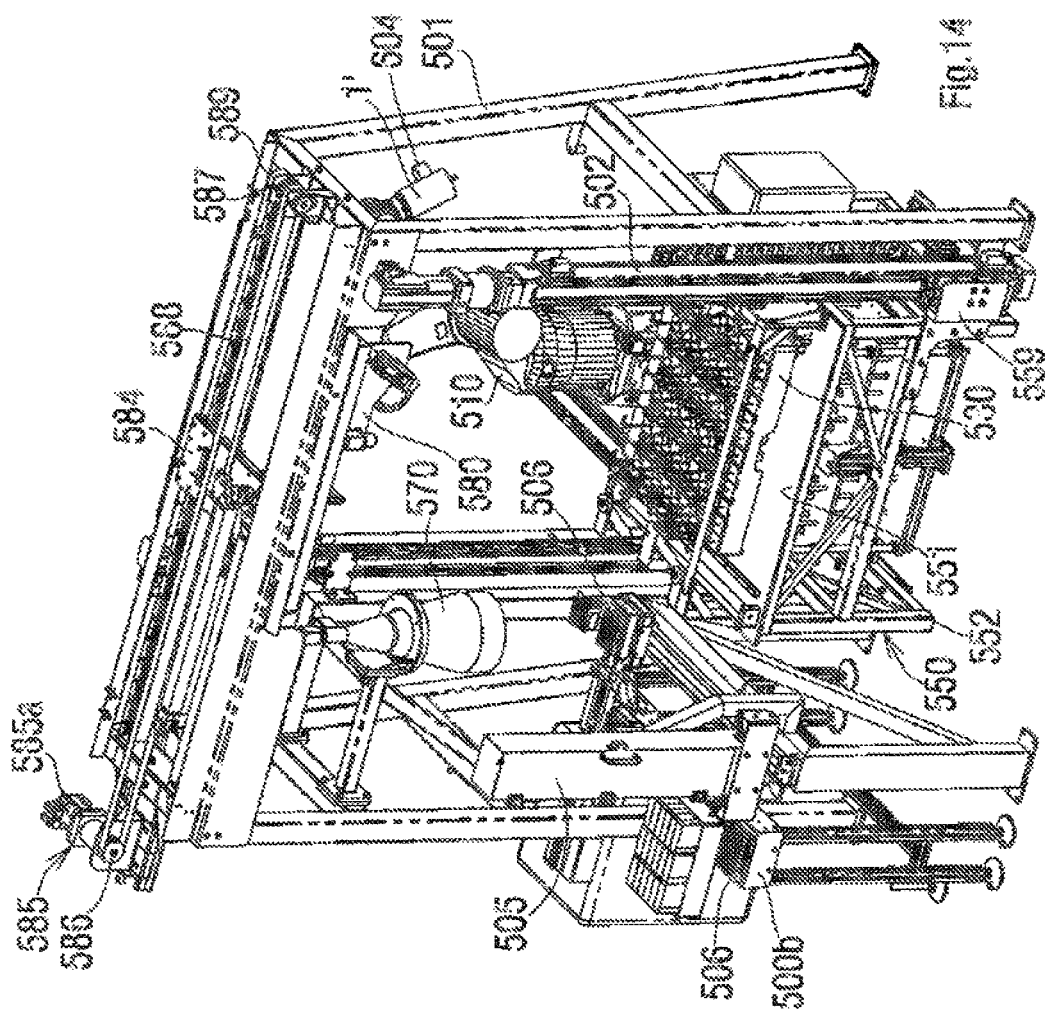

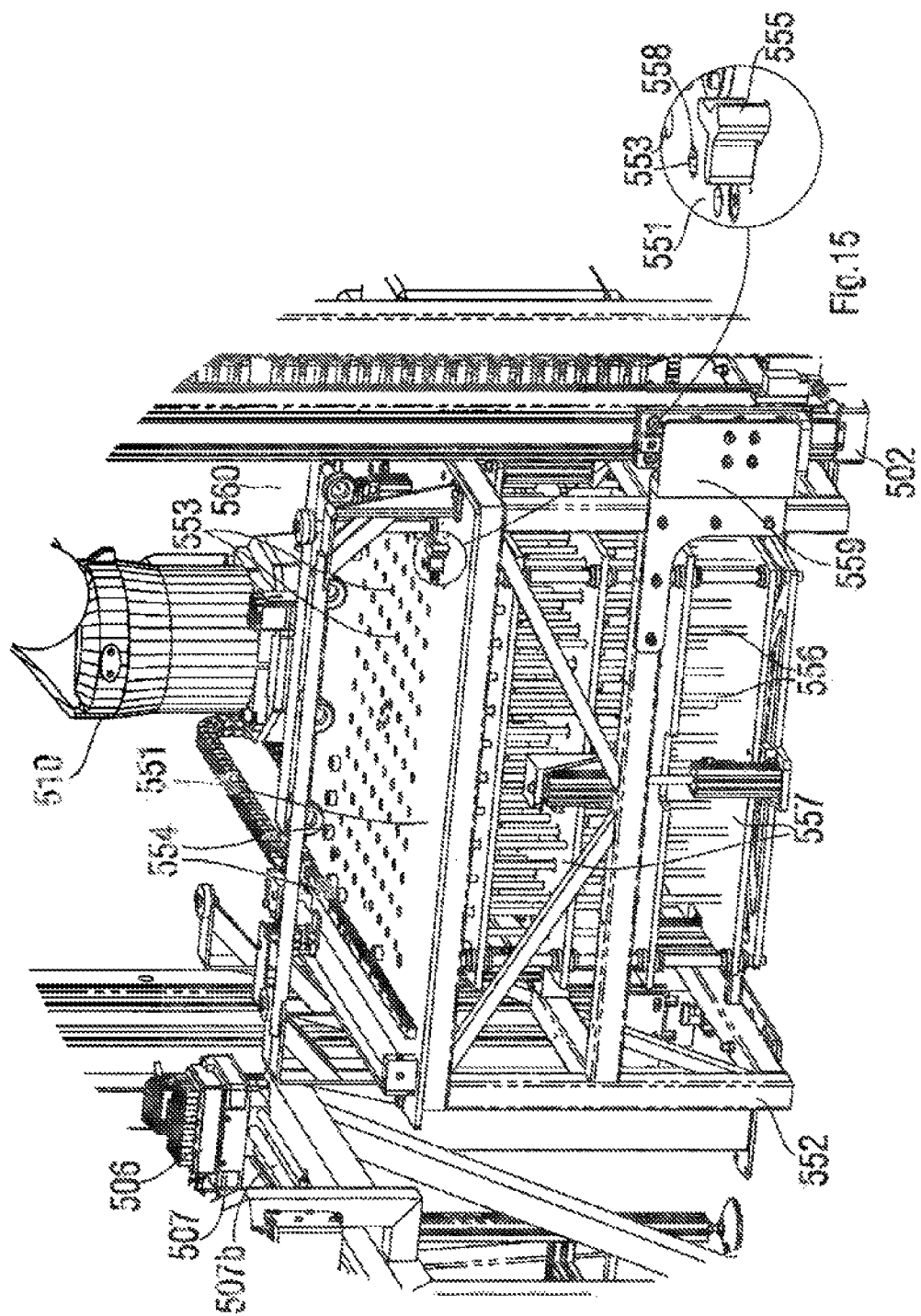

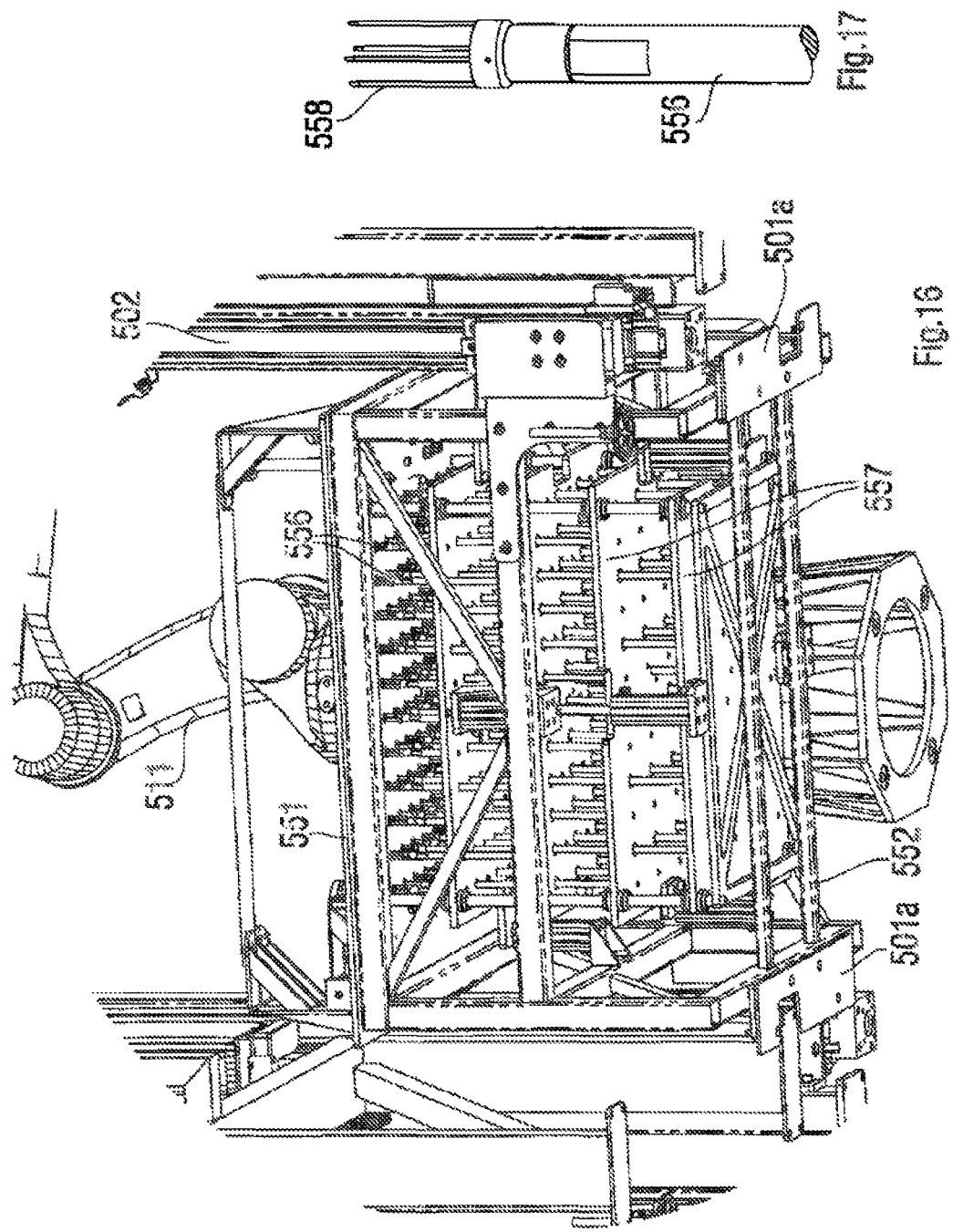

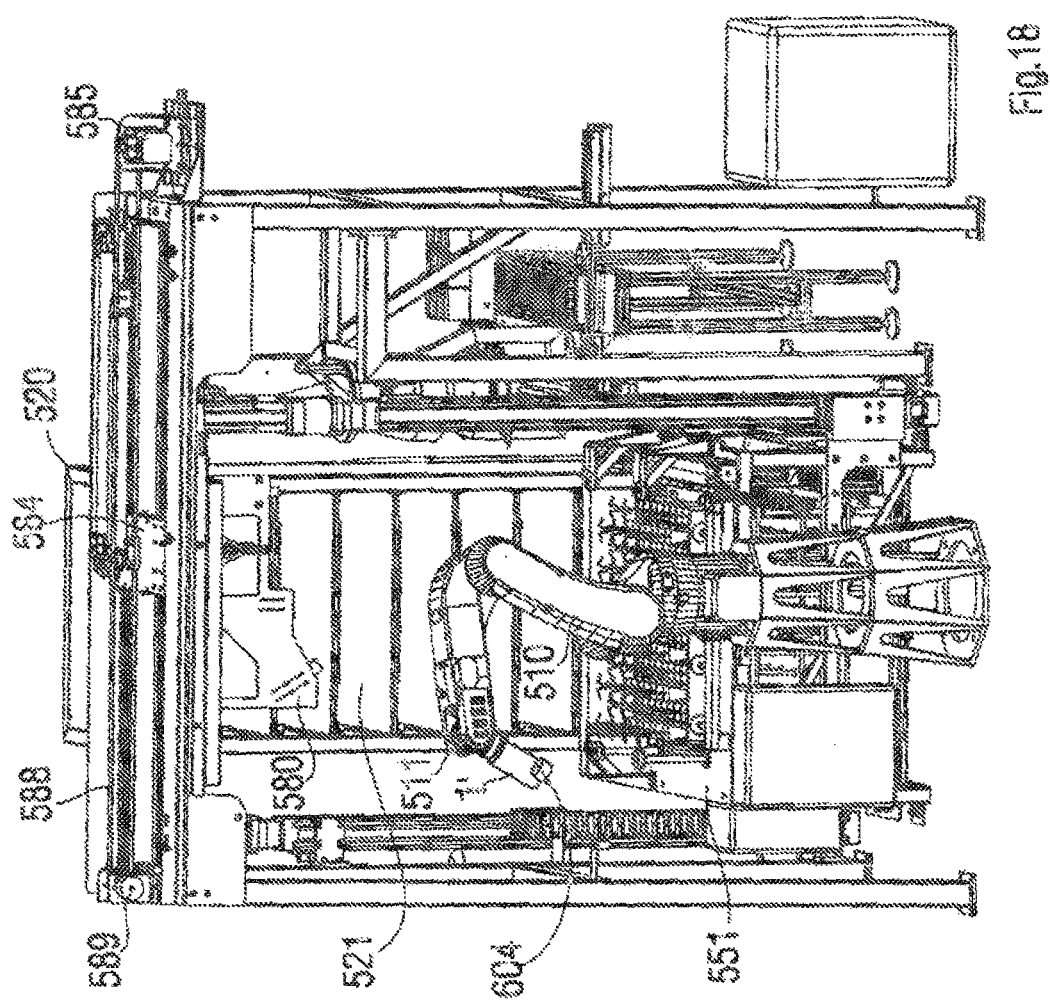

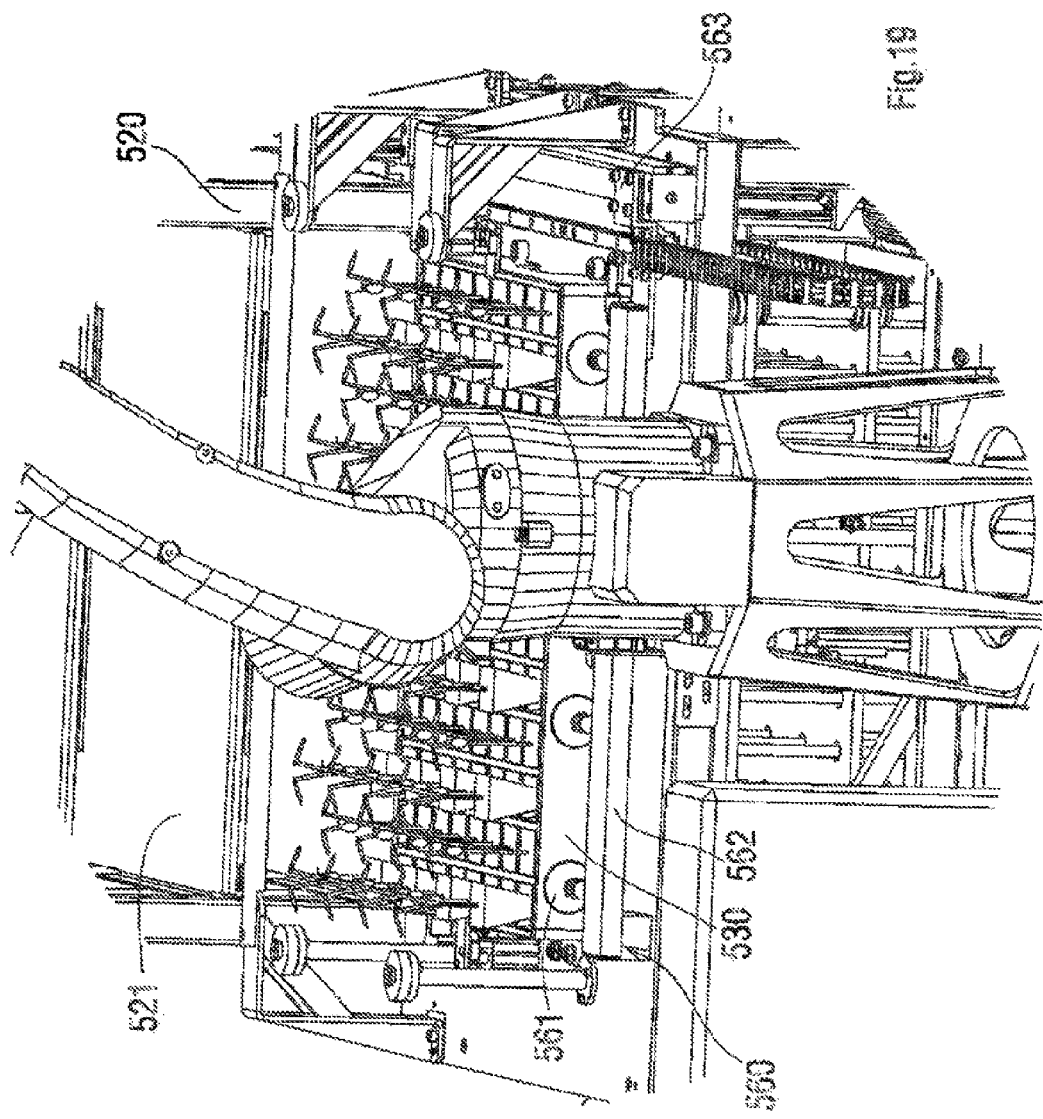

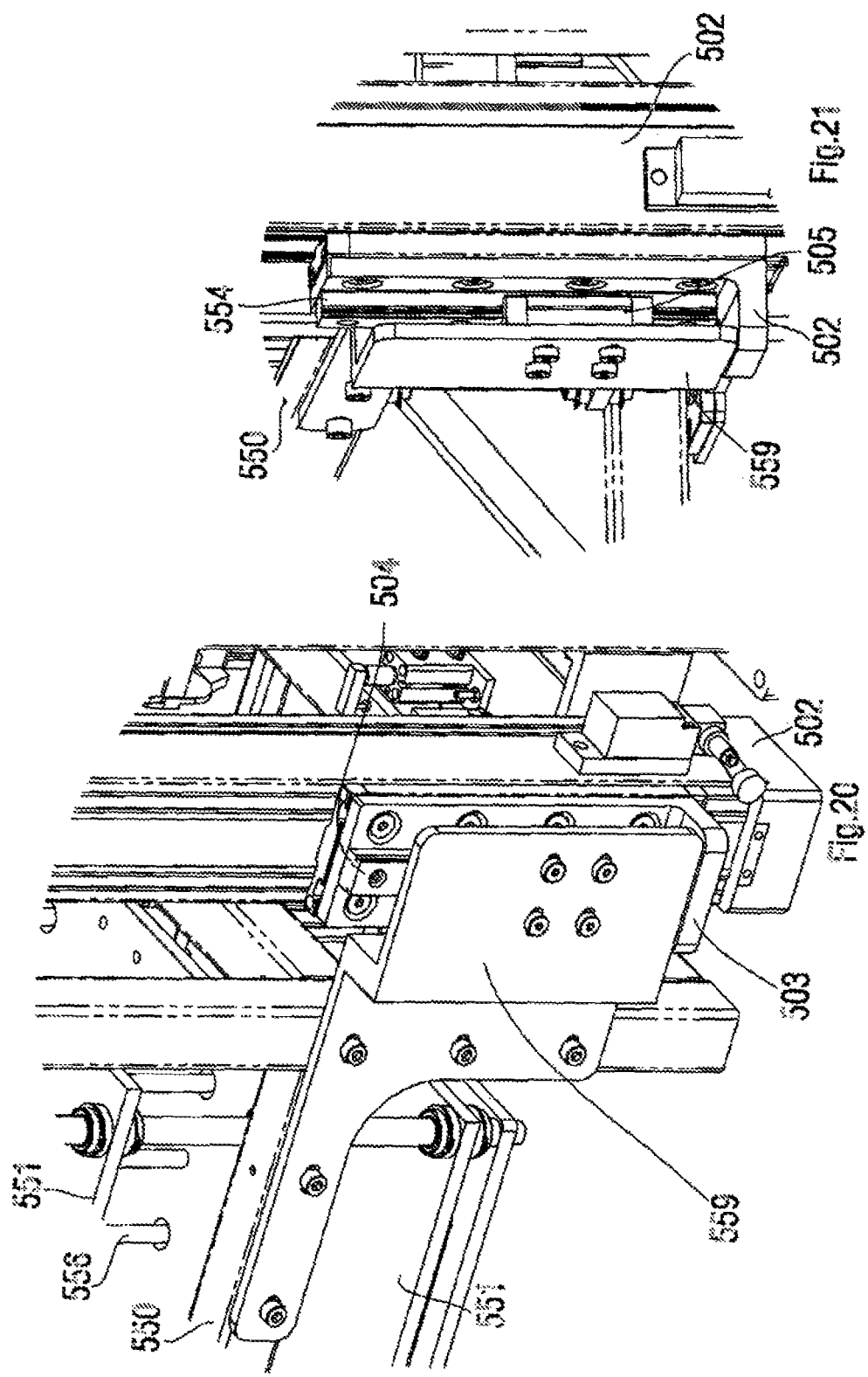

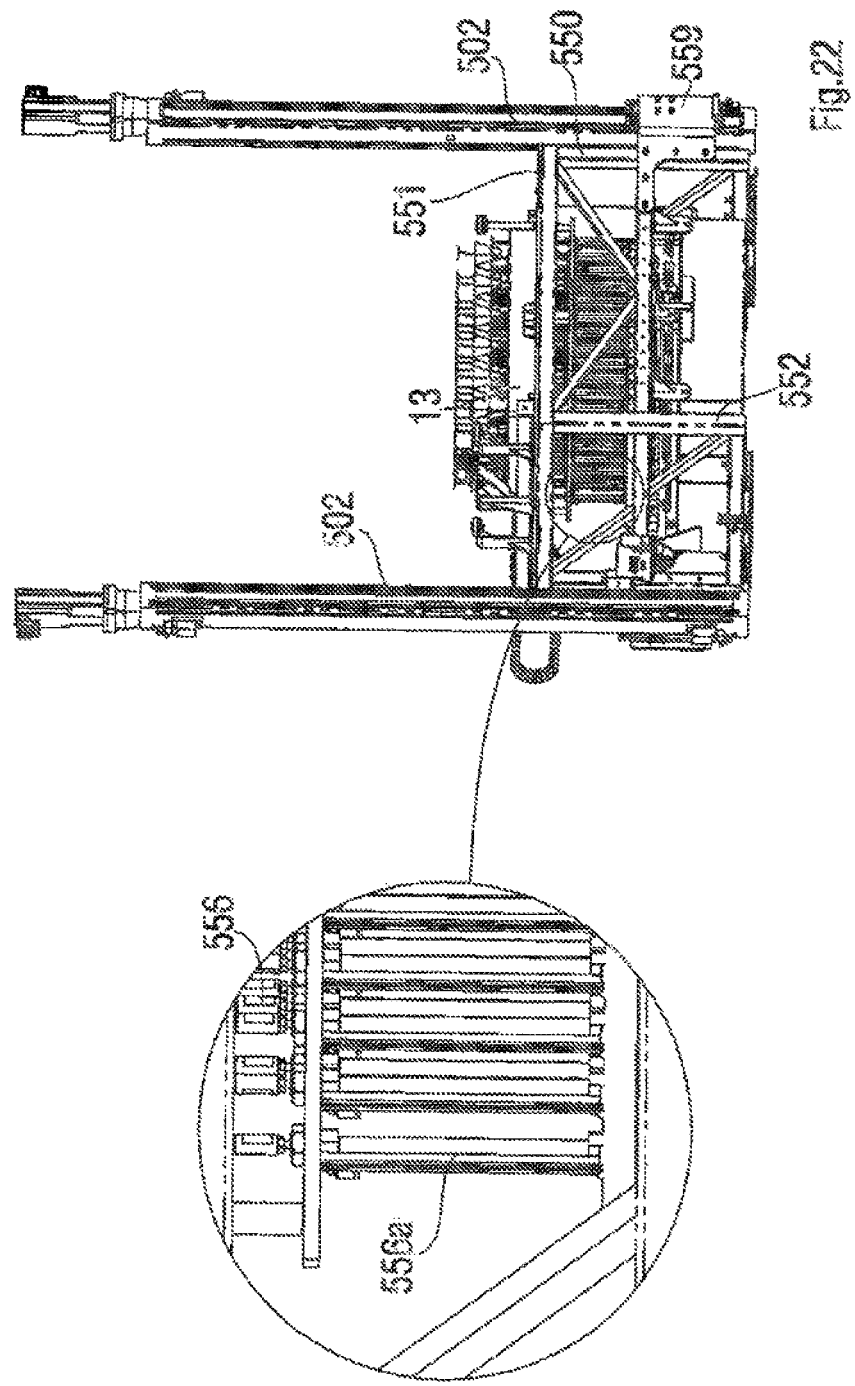

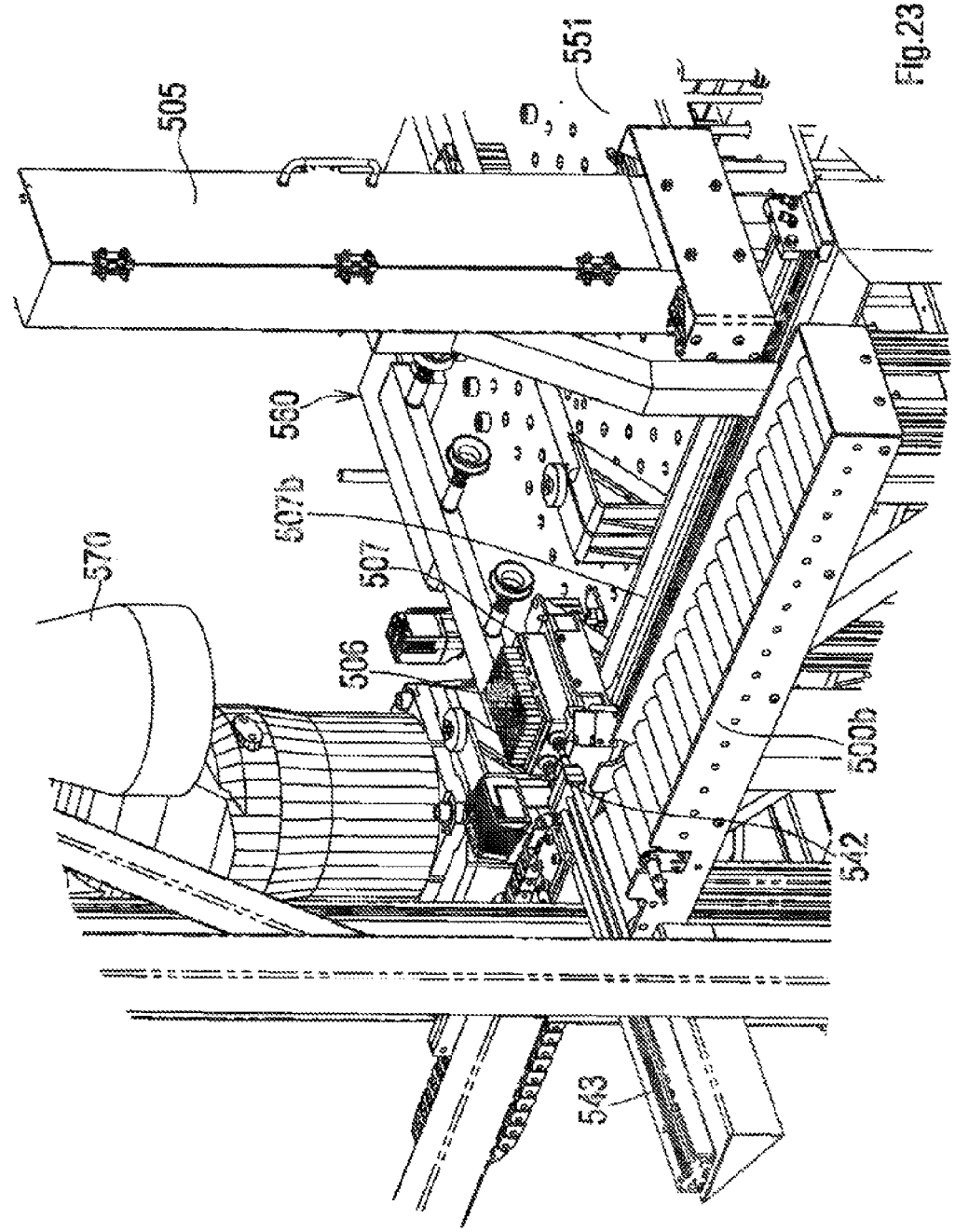

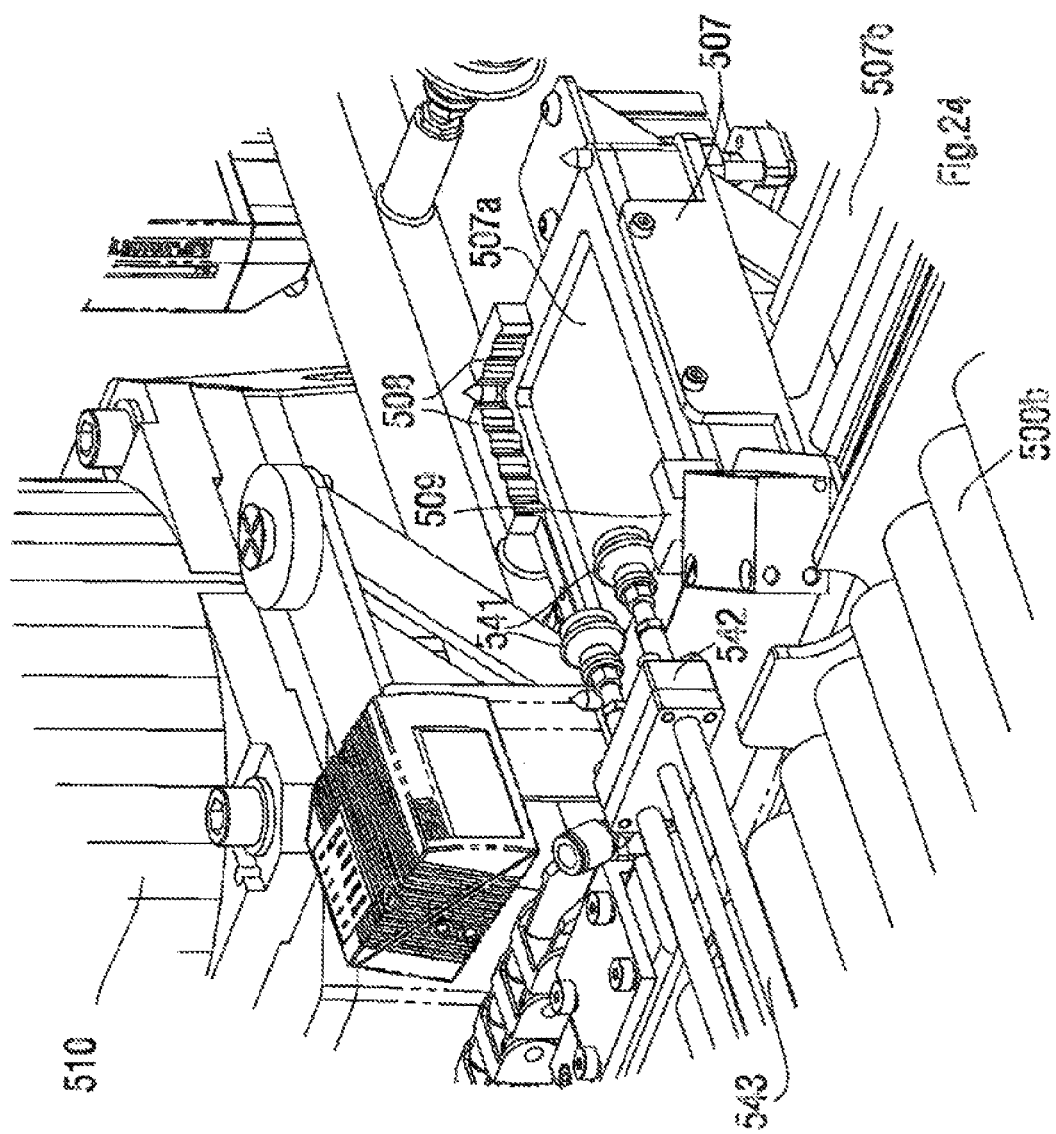

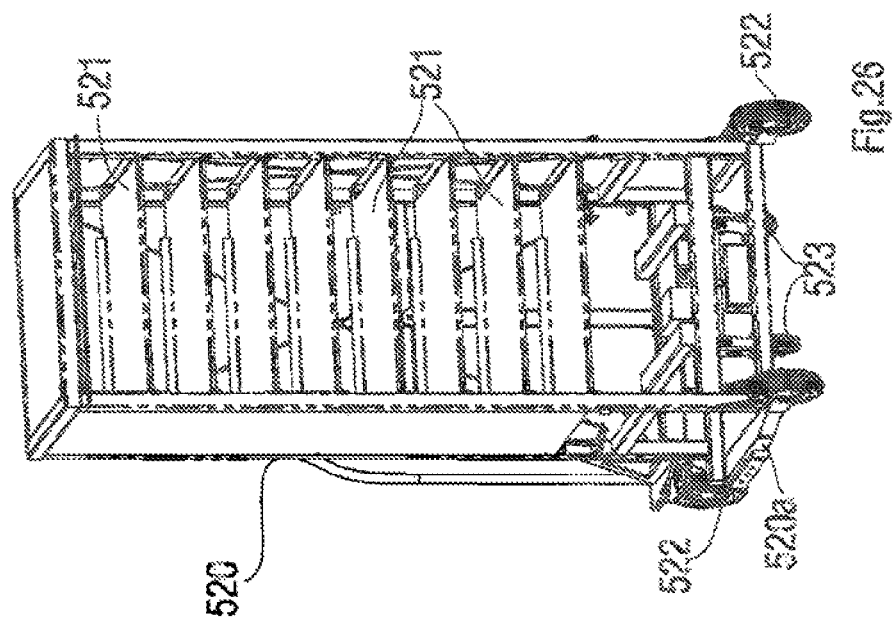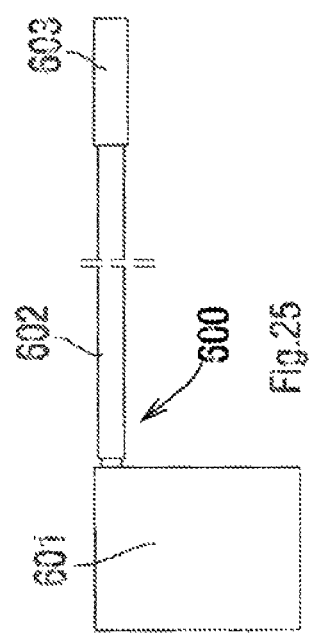

TOOL FOR SAMPLING PLANT MATERIAL, AUTOMATION COMPRISING SAME, SAMPLING CELL PROVIDED WITH SUCH AN AUTOMATION AND SAMPLING METHOD

RELATED APPLICATIONS

This application is a §371 application from PCT/FR2013/052373 filed Oct. 7, 2013, which claims priority from French Patent Application No. 12 59526 filed Oct. 5, 2012, each of which is herein incorporated by reference in its entirety.

TECHNICAL FIELD

The present invention belongs to the field of the equipment used for example to cut a plant sample to be analyzed from one of the leaves of a plant. More particularly, the present invention relates to a tool for taking a sample, for example, of a plant, of a seedling or of a part of a plant, preferably from a leaf or a cotyledon, more preferably from the first leaf, for the purposes of genetic analyses, even phenotypic analyses, or even pathological analyses (identification of the presence of a viral, bacterial, fungal or other parasite).

BACKGROUND OF THE INVENTION

It is known that the business of selecting and improving plants involves the use of the most efficient genetic analysis technologies, identifying as rapidly as possible the plants, notably at the stage of seedlings carrying the genetic combinations of interest. These analyses are carried out from tissue samples of the plants, followed by DNA extraction which will then be analyzed. Similarly, the business of selecting and improving plants implies pathological analysis capabilities: the plants are subject to viral, bacterial or even fungal attacks and it may be necessary to identify these attackers, for example by means of DNA analyses, by sampling from the plant tissues. However, the genetic analysis of the plants, even of their attackers, faces a bottle neck, not in terms of analysis capacity, but in terms of the capacity to supply plant material to be analyzed. In other words, the laboratories generally have the capacity to perform a number of genetic analyses far greater than they do today, provided that they receive sufficient samples of plant material to be processed.

In the laboratories, the technicians now in charge of this task are at the maximum of their capabilities, devoting all their time to collecting samples when they could be employed in more qualified tasks. Furthermore, such repetitive work, presenting a significant level of stress, leads to a certain percentage of errors which can falsify the identification of the plants of interest. Furthermore, the uniformity of the samples risks varying over the course of the operations. In addition, there are risks of pollution of the sample by incorrect handling.

Some automated sampling technique solutions exist, such as, for example, "seed chipping" (automated taking of a biological sample from a seed, for example a seed of corn), but they are not suited to the small size of most of the seeds of the garden species (tomato, lettuce, etc.) and of certain species of large crops (rape seed for example).

OBJECT AND SUMMARY OF THE INVENTION

The object of the present invention is to propose a tool that makes it possible to rapidly and non-destructively take a large number of samples of plant material.

To this end, the tool for sampling, preferably, plant tissues according to the invention is essentially characterized in that it comprises:
- a guiding body provided with a through bore,
- a part-holding punch mounted with sliding adjustment in the through bore of the guiding body,
- a part-holding die, secured to the guiding body, positioned under the latter and separated from said body by an opening for introducing the plant to be cut, said die being provided, in the axial alignment of the through bore of the guiding body, with a through bore into which the bottom end of the punch penetrates when cutting plant tissue to be sampled.
- a means for actuating the punch between an initial position whereby it is retracted into the guiding body, an intermediate position whereby the punch, by its bottom end, is situated in the bore of the die, and a final position whereby it passes right through the die and whereby its bottom end, it is outside the through bore of the die.

Such arrangements have the effect of mechanizing the taking of plant samples, without risk of error and automatically.

The initial position of the punch corresponds to a position in which the opening is freed for the introduction therein of the plant material. In the intermediate position of the punch, the plant sample is situated in the bore of the die and is kept there essentially by friction. In this position, the support of the sampling tool can be displaced at high speed from the sample-taking area to an area of delivery thereof. The final position of the punch corresponds to the position of delivery of the cut sample. In this position, the tool is positioned above the delivery area and more particularly above an appropriate container provided to receive the sample.

To facilitate the ejection of the sample, according to another feature of the invention, the tool provides means for ejecting a gaseous fluid or a liquid fluid or a mixture of the two at the bottom end of the punch.

According to another feature of the invention, these ejection means comprise a gaseous and/or liquid fluid feed head, an internal channel for dispensing a gaseous and/or liquid fluid, formed in the punch, interconnected with the feed head and at least one nozzle formed in the bottom part of the punch and emerging in the bottom face thereof, said nozzle being interconnected with the internal channel of the punch.

According to another feature of the invention, the internal channel receives a cannula for dispensing gaseous and/or liquid fluid, interconnected on the one hand with the feed head and on the other hand with the or each nozzle.

According to another feature of the invention, the diameter of the cannula is smaller than the diameter of the channel in order to form, between said cannula and said channel, a pathway for the gaseous and/or liquid fluid, this pathway being interconnected on the one hand with the feed head and on the other hand with the or each nozzle of the punch.

According to another feature of the invention, the opening for introducing the plant is flared. This arrangement facilitates the placing of the plant material in the opening.

According to a practical embodiment, the introduction opening is limited by a bottom horizontal face, corresponding to the top face of the die, by a top oblique face, corresponding to the bottom face of the guiding body and by a rear vertical face of a wall linking the die to the guiding body.

According to another feature of the invention, the trajectory of the punch is tangential to the rear vertical face of the opening and the through bore of the die is tangential to a geometrical plane containing said rear face in order to produce, in the plant from which the sample is taken, a cut with open contour.

According to another feature of the invention, the cross section of the bottom part of the punch and the cross section of the bore of the die each have, considering the movement in introducing the plant into the opening which is performed from front to rear, a front part and a rear part, the front part being wider than the rear part.

In combination with this feature, the contour of each rear part of the cross sections of the bottom part of the punch and of the bore of the die is tangential to a geometrical plane containing the rear face of the opening.

These arrangements make it possible to cut the sample at a distance from the edge of the leaf and to produce a cut with open contour facilitating the removal of the sampling tool without damaging said plant.

Another subject of the present invention is an automatic machine for taking samples comprising a manipulating arm, possibly multi-axial, bearing the sampling tool according to the invention.

Also the subject of the present invention is an automated cell for taking samples comprising a bearing structure receiving the plants to be analyzed, possibly a support table that can be displaced height-wise facing the bearing structure and possibly a deck transfer system between the support structure and the table, characterized in that it comprises a sampling tool according to the invention.

According to another feature of the invention, the cell further comprises a line for supplying containers intended to receive the samples taken by the tool.

Another subject of the present invention is an automated cell for taking samples. Such a cell is essentially characterized in that it comprises:
- a support table designed to receive cellular trays bearing plants in clods of earth to be sampled,
- an automatic machine provided with a manipulating arm, and,
- a sampling tool according to the invention borne by the manipulating arm of the automatic machine.

According to another feature of the invention, the support table of the cell comprises a transfer system for cellular trays, suitable for ensuring the transfer of the cellular trays between the support table and a means for transporting cellular trays and vice versa.

According to another feature of the invention, the support table can be displaced height-wise facing the transport means.

Another subject of the present invention is a cellular tray transport means suitable for ensuring the transportation of said trays from a plant storage and/or growth area, to the sampling cell, and vice versa, from said cell to said storage and/or growth area.

The plant storage and/or growth area can consist of a greenhouse, or any other enclosure specifically for storing and/or growing plants.

According to another feature of the invention, the transport means consists of a transport carriage provided with evenly spaced horizontal shelves fixed to the frame and two sets of rolling members, one of which is borne by a raising and lowering system.

Another subject of the present invention is a method for taking a sample comprising:
a) moving the tool toward a previously selected plant or alternatively moving the plant toward the tool,
b) engaging the opening on either side of one of the leaves of this plant,
c) cutting a sample by punching the leaf and doing so by moving the punch from its initial position to its intermediate position,
d) keeping the punch of the tool in the intermediate position, in order to keep the sample in the through bore of the die,
e) removing the tool or alternatively the plant, while ensuring that the punch of the tool is kept in the intermediate position,
f) depositing the sample in an appropriate and dedicated container.

Another subject of the present invention is a method for analyzing samples comprising:
a) moving the tool toward a previously selected plant or alternatively moving the plant toward the tool,
b) engaging the opening on either side of one of the leaves of this plant,
c) cutting a sample by punching the leaf and doing so by moving the punch from its initial position to its intermediate position,
d) keeping the punch of the tool in the intermediate position, in order to keep the sample in the through bore of the die,
e) removing the tool or alternatively the plant, while ensuring that the punch of the tool is kept in the intermediate position,
f) depositing the sample in an appropriate and dedicated container,
g) analyzing the samples, notably analyzing their DNA.

The techniques for extracting DNA and then analyzing them, for example by means of molecular markers, are known to those skilled in the art of molecular biology. They are for example described in the patent application FR 07/01589, the DNA there being obtained by a CTAB (Cetyl Trimethylammonium Bromide)/chloroform extraction and the molecular marking being performed by means of CAPS (Cleaved Amplified Polymorphic Sequence) and SCAR (Sequence Amplified Characterized Region) markers. The term "molecular marker" should be understood to mean a specific fragment of a DNA sequence that can be identified within a genome of an individual and that can notably be used to locate a gene of interest, verify whether an individual has inherited a particular characteristic of a parent or differentiate two individuals. It may or may not be a coding sequence. The marker can be dominant, co-dominant. The detection of the molecular marker, or its non-detection, makes it possible to select the individuals that exhibit the gene of interest or the particular characteristic, or, on the other hand, to not select the individuals who do not exhibit the gene of interest or the particular characteristic. In the present invention, the molecular markers make it possible to rapidly test the plants or seedlings during development and retain those which have the characteristics sought. Molecular markers of different kinds are known to those skilled in the art: AFLP (amplified fragment length polymorphisms), SCAR (sequence characterized amplified region), SSR (microsatellites, or simple sequence repeats), RFLP (restriction fragment length polymorphisms), etc.

Yet another subject of the present invention is a method for selectively eliminating plants that do not comprise the genetic element or elements sought, for example molecular markers, said method comprising:
a) moving the tool toward a previously selected plant or alternatively moving the plant toward the tool,
b) engaging the opening on either side of one of the leaves of this plant, c) cutting a sample by punching the leaf and doing so by moving the punch from its initial position to its intermediate position, d) keeping the punch of the tool in the intermediate position, in order to keep the sample in the through bore of the die, e) removing the tool or alternatively the plant, while ensuring that the punch of the tool is kept in the intermediate position, f) depositing the sample in an appropriate and dedicated container, g) analyzing the samples, notably analyzing their DNA, h) destroying plants by a plant suction system during a second run of the cellular trays in the automated sampling cell.

According to another feature common to the three methods as explained above, the depositing of the sample is performed by movement of the punch of the sampling tool from its intermediate position to its final position.

According to another feature, the depositing of the sample is performed by ejection of a fluid.

This fluid can be a gas or a liquid or even a mixture of the two.

The ejection of the fluid can constitute an alternative to the deposition of the sample by moving the punch, but this ejection can be combined with the movement of the punch between the intermediate position and the final position.

According to another feature common to the three methods as explained above, a cut with open contour is produced in the plant that is tangential or secant to one of the edges of said plant.

BRIEF DESCRIPTION OF THE DRAWINGS

Other aims, features and advantages of the invention will become apparent on reading the description of a preferred embodiment, given as a nonlimiting example with reference to the attached drawings, in which:

FIG. 3 is a view in cross section of a feed head of the tool according to the first embodiment, notably ensuring the mechanical link between the motor means and the punch, FIG. 4 is a view of the punch from below, FIGS. 5 to 7 illustrate the mode of operation of the tool according to the first embodiment of the invention, FIG. 13 is a perspective view of an automated sampling cell according to the invention, FIG. 14 is a perspective view of this same cell without the elements of the enclosure and without the means for transporting the cellular trays bearing the plants or seedlings to be sampled, FIGS. 15 and 16 are partial views of the cell, in perspective, showing the support table, FIG. 17 is a partial view of a lifting rigid rod with which the support table is equipped, FIG. 18 is a perspective rear view of a sampling cell, FIG. 19 is a perspective rear view of the support table, FIGS. 20 and 21 are perspective views showing the means for lifting the support table, FIG. 22 is a perspective view of a support table according to another embodiment, FIGS. 23 and 24 show the means for supplying sampling boxes, and a pod for transporting sampling boxes to an area for parking and collecting the samples taken, the sampling box not being represented in FIG. 24, FIG. 25 is a schematic view of a means for eliminating plants in clods of earth by suction, FIG. 26 is a perspective view of a transport carriage.

DETAILED DESCRIPTION OF THE EMBODIMENTS

Figure 1:
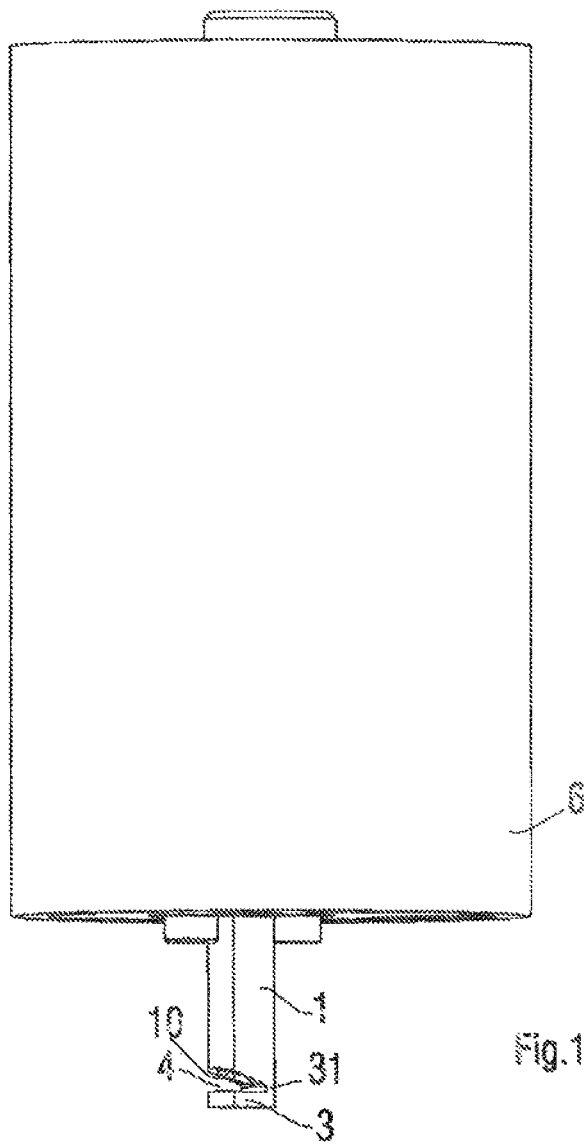
FIG. 1 is a perspective view of a first embodiment of a sampling tool according to the invention.
Figure 2:
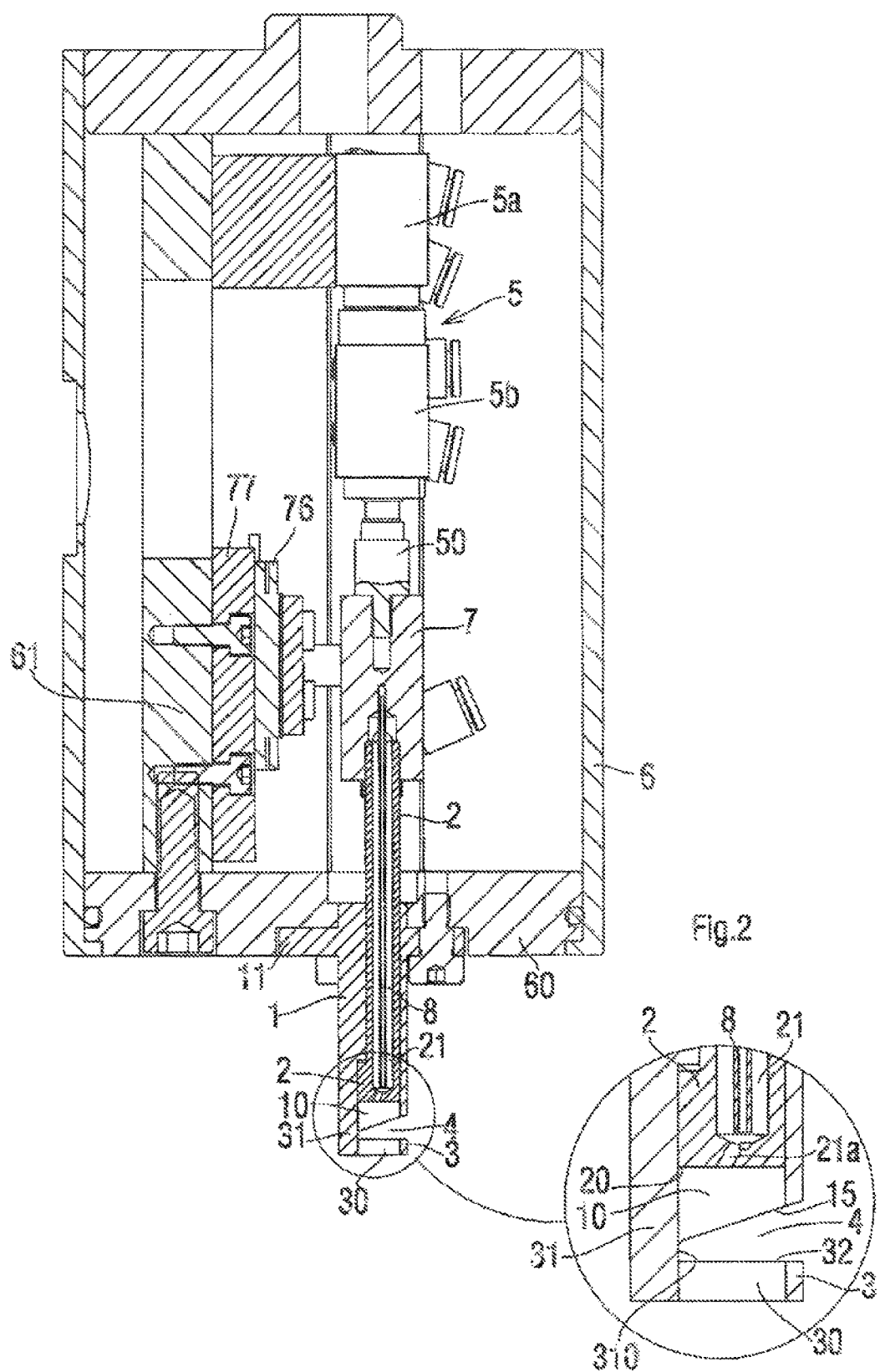
FIG. 2 is a view in longitudinal cross section of the tool according to its first embodiment.
Figure 8:
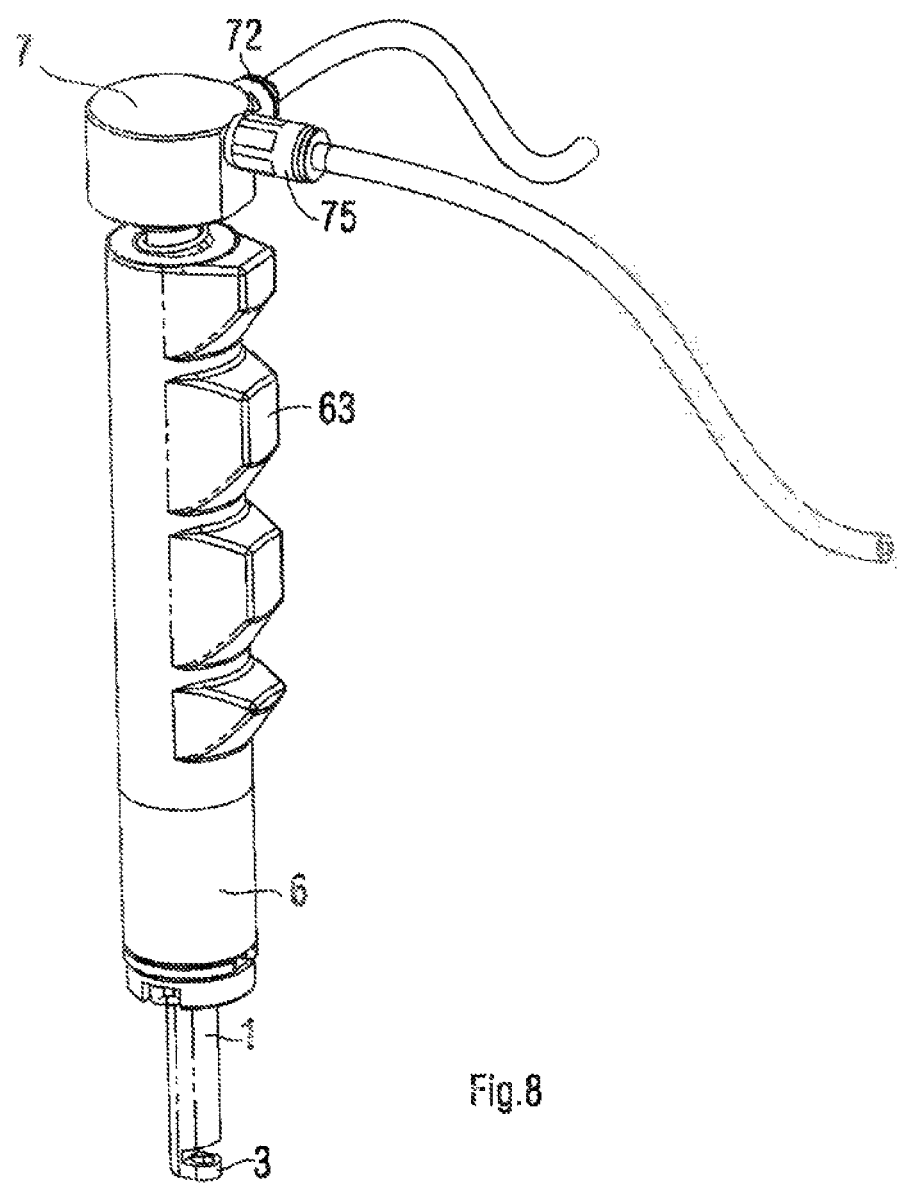
FIG. 8 is a perspective view of a variant embodiment of the tool according to the invention.
Figure 9:
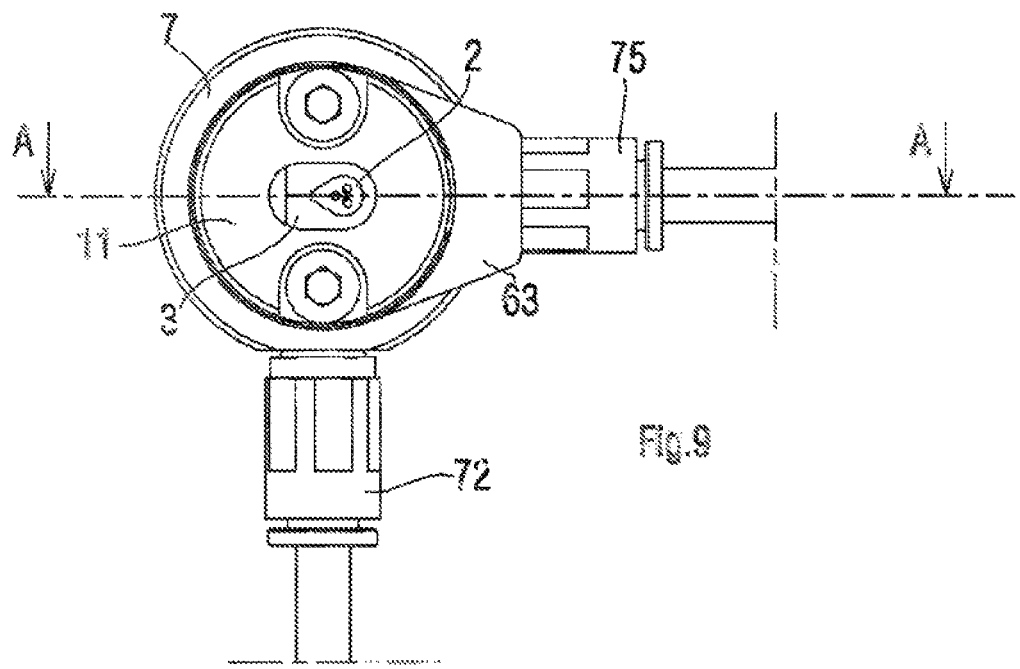
FIG. 9 is a view from below of the tool according to the variant embodiment.
Figure 11:
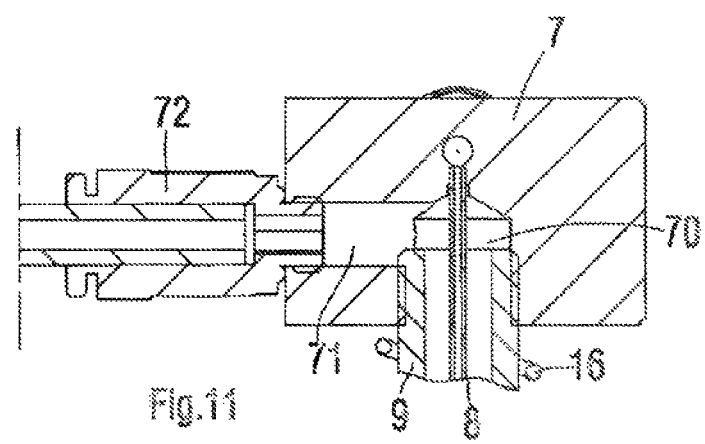
FIG. 11 is a view in longitudinal cross section along the line BB of FIG. 9.
Figure 10:
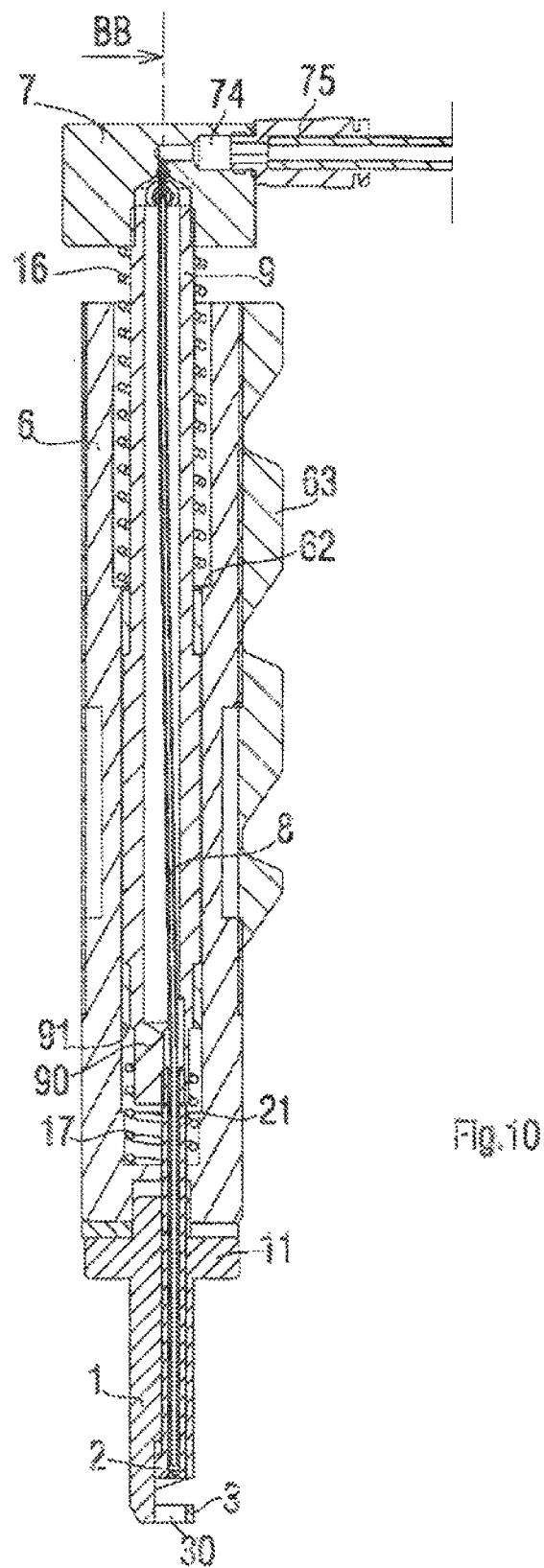
FIG. 10 is a view in longitudinal cross section along the line AA of FIG. 9.

In the present description, "sampling" should be understood to mean the action consisting in taking, by cutting, a sample from a plant.

FIGS. 1 to 4 show a tool according to a first embodiment. As represented in these figures, the sampling tool according to the invention is designed to be borne, for example at the end of a multi-axial manipulating arm that is known per se. It can be borne by any other mechanized system with several degrees of freedom, suitable for moving it in all three directions and all three orientations of space. This tool, according to a variant embodiment, is borne by an operator and is manipulated and actuated by this operator.

The tool 1' according to the invention comprises a vertical longiform guiding body 1 provided with an axial through bore 10 in which a part-holding punch 2 is mounted with sliding adjustment. The tool also comprises, under and at a distance from the bottom end of the guiding body 1, a part-holding die 3 secured to the guiding body by a wall 31. This die 3 is thus separated from the bottom end of the guiding body by an opening 4 for introducing the plant to be cut.

The part-holding die 3, in the axial alignment of the through bore 10 of the guiding body 1, is provided with a through bore 30, of constant cross section, into which the bottom end of the punch penetrates when cutting the plant sample to be taken from the leaf previously introduced into the opening 4. The bottom end 20 of the punch 2 and the bore 30 of the die have, with a functional play, identical cross sections in terms of contours and dimensions.

The tool 1' according to the first embodiment also comprises a motor means 5 for actuating the punch 2 between an initial position whereby it is retracted into the guiding body 1, an intermediate position whereby, by its bottom end 20, it is situated in the bore 30 of the die 3, and a final position whereby it passes right through the die 3 and whereby its bottom end 20 is outside the through bore 30 of the die. This motor means 5 comprises an output element 50 with linear displacement, on which an effort and a displacement movement are available. This output element takes the form of a rigid rod.

According to a practical embodiment, the guiding body 1 comprises, at the top end, a plate 11 for fixing to the bottom base 60 of a protective casing 6 notably enclosing the motor means 5. The base 60, in the axial extension of the through bore 10 has a through hole for the passage of the punch 2. This protective casing 6 is provided with means, known per se, for fixing to the manipulating arm.

Preferentially, the tool 1', in its two embodiments, is provided with means for ejecting a gaseous fluid or a liquid fluid or a mixture of the two at the bottom end of the punch. These means make it possible to eject the sample taken and are described hereinbelow. The part-holding punch 2 comprises an internal channel 21 emerging at its top end to be interconnected with a gaseous and/or liquid fluid feed head 7. In the bottom part, this internal channel 21 is interconnected with at least one nozzle 21a formed in the bottom part of the punch and emerging in the bottom face thereof.

According to the preferred embodiment, the punch comprises, in the bottom part, three nozzles 21a preferably extending obliquely relative to the longitudinal axis of the internal channel.

These provisions make it possible to inject, into the bottom part, a fluid in gaseous form and/or a liquid to facilitate the ejection of the sample. The nozzles 21a of this channel 21, in the bottom part, make it possible to distribute the gaseous and/or liquid fluid over a number of areas of the sample and thus facilitate its ejection.

Similarly, this channel 21 and the nozzles 21a can be subjected to a slight vacuum pressure in order to ensure that the sample is kept at the bottom end of the punch 2, upon the movement of the tool 1' from the sampling area to the depositing area.

According to the first embodiment of the tool 1', the feed head 7 is fixed to the motor means 5 and more particularly to the output element 50 thereof. This head 7 therefore ensures the transmission of movement between the output element 50 of the motor means 5 and the punch 2.

This head 7 according to the two embodiments of the tool 1' has a first cylindrical axial boring 70 interconnected with the channel 21 of the punch, this first axial boring 70 being interconnected via a first radial boring 71 with an end-fitting 72 fixed to the feed head and coupled to a source of gaseous and/or liquid fluid, for example a compressed gas, via a duct and a solenoid valve that are not represented. According to the first embodiment of the tool 1', the top part of the punch 2 is fixed in a seal-tight manner in the first boring 70. It can be noted that the radial boring 71 emerges in the cylindrical boring 70 above the punch.

In the final position of the punch 2, the solenoid valve is activated in the direction of the opening in order for the compression gas, in this case air, to be introduced into the channel 21 of the punch 2. The ejection of this compressed air, through the nozzles 21a of the channel at its bottom end, makes it possible to drive out the sample taken. This sample is intended to be collected by any appropriate container, for example of the type of those marketed by the company QUIAGEN under the reference "Collection Microtubes Nonsterile polypropylene tubes".

In order to activate the solenoid valve when the punch 2 reaches its final position, at least one position sensor is provided, of the inductive type for example. This sensor is suitable for detecting the final position of the punch 2 and for generating a signal in response. This signal has the effect of activating the solenoid valve in order for the pressurized air to be delivered. It should be noted that the pressurized air is delivered in the form of a pulse.

The channel 21, according to a preferred embodiment, is equipped with a cannula 8 for dispensing gaseous or liquid fluid. As can be seen, this cannula 8 extends axially in the channel 21 and has a diameter very much smaller than the diameter thereof. Thus, around the cannula 8, a sufficient passage is freed up for the gaseous or liquid fluid. This cannula 8, by its internal channel, is interconnected with a second cylindrical axial boring 73 formed in the feed head 7, preferably in the axial extension of the first boring 70. This second boring 73 is interconnected via a second radial boring 74 with a second end fitting 75. This end-fitting, fixed to the head 7, is coupled to this source of gaseous and/or liquid fluid via a duct and a solenoid valve that are not represented. In the preferred embodiment, the cannula, by its top end, is engaged in a seal-tight manner in the second axial boring 73.

As indicated previously, the opening of the solenoid valve in order for the liquid and/or gas to be delivered and ejected at the end of the punch will be triggered by the signal generated by the position sensor. It should be noted that this delivery and ejection of liquid and/or gas takes the form of a pulse.

It should be noted that the second radial boring 74 emerges in the second axial boring 73 above the dispensing cannula 8.

Advantageously, the feed head 7 is equipped with a slide 76. This slide 76 is engaged slidingly on a vertical rail 77 secured to a vertical plate 61 mounted fixedly on the base 60.

The opening 4 has, for example, a flared form to facilitate the introduction of the plant material. As can be seen, this opening 4 is limited by a top horizontal face 32 of the die 3, by a bottom oblique face 15 of the guiding body and by a rear vertical face 310 belonging to the wall 31.

Preferably, the cross section of the bottom part of the punch 2, and the cross section of the bore of the die each have a front part and a rear part, the front part being wider than the rear part. The front part is defined as being that furthest away from a geometrical plane containing the rear vertical face 310.

According to a practical embodiment, the contour of each front and rear part is established along a curve, for example a circumferential arc of circle, the radius of curvature of the front part being greater than the radius of curvature of the rear part. These front and rear contours are joined by straight segments.

In combination with these features, the contour of each of the rear parts of the straight sections of the bottom part of the punch and of the bore of the die is tangential to a vertical geometrical plane containing the rear face 310 of the opening 4. This arrangement, when cutting the sample, makes it possible to form, on the plant material (in this case one of the leaves of a plant), a contour that is open to the rear making it possible to remove the tool 1' without damaging the leaf, this removal being performed when the punch 2 is in the intermediate position.

Advantageously, the motor means 5 of the tool 1' according to the first embodiment is formed by two motor members, for example pneumatic 5a, 5b, arranged in series, aligned along a vertical axis. The top motor member 5a is fixed to the rear plate 61. This motor member 5a is provided with an output element with linear displacement, in the form of a rod. The output element of the motor member 5a is rigidly fixed to the yoke frame of the motor member 5b, the latter being borne by the motor member 5a. The output element of the motor member 5b constitutes the output element 50 of the motor means 5.

The desactivated state of the two motor members 5a, 5b corresponds to the initial position of the punch 2, whereas the activated state of one of the two motor members 5a, 5b, for example the motor 5a, corresponds first to the plant sample cutting movement and to the keeping of the punch 2 in the intermediate position. The simultaneous activation of the two motor members 5a, 5b and the keeping of these motor members in this state corresponds to the final position of the punch 2.

Referring to FIGS. 5 to 7, there now follows an explanation of the operation of the tool 1' according to the invention.

The tool 1' is displaced toward a previously selected plant and the opening 4 is engaged on either side of one of the leaves F of this plant (FIG. 5). According to an alternative, it is the plant which is displaced toward the tool 1'. During this approach and positioning movement, the two motor members 5a, 5b are deactivated and the punch 2 is kept in the initial position. Next, the motor member 5a is activated in order to perform a cutting operation of a sample E by punching the leaf F (FIG. 6). The punch 2 is then brought to and kept in the intermediate position (FIG. 6). In this position, the sample E is housed in the bore 30 of the die 3 and is protected thereby. Still while ensuring that the punch 2 is kept in the intermediate position, the tool 1' is driven by a retraction movement to be disengaged from the punched leaf F. Alternatively, the plant is driven by a retraction movement to disengage the punched leaf F from the tool 1'. Since the contour of the cut on the leaf is open, the banks of this cut will be able to be easily separated from one another to slide over the punch 2. Such an arrangement avoids any pulling force damaging to the leaf and to the plant. After removal, the sampling tool 1' is displaced to an area of delivery or of deposition of the sample. Alternatively, the area of deposition of the sample, for example a suitable container, is displaced toward the tool 1'. For this deposition, the two motor members are activated and the punch 2 is driven toward its final position (FIG. 7). The sample E borne by the bottom end of the punch 2 is located outside the bore 30 of the die 3 to be deposited in an appropriate container, for example a tube borne by a sampling box. In the final position of the punch, the solenoid valve associated with the compressed gas circuit or with the pressurized liquid circuit is activated so as to drive the sample E toward the dedicated container.

After sampling, the sampling boxes containing the samples, and more particularly the containers or wells, can be closed by means of suitable lids containing silica gel (or another product having the capacity to control the humidity), to allow them to dry. Such an arrangement is mainly used to prevent the degradation of the samples taken. They can thus be transported or stored without risks of deterioration of the tissues. This method avoids, for example, the constraints of keeping cold to conserve the tissues or the use of a lyophilizator. The use of silica gel to dry plant tissues is, for example, described in the paper by Chase and al., (Taxon, Vol. 40, No. 2, May 1991) where the silica gel is placed directly in the hermetically sealed bags containing the samples. In the case of the present invention, the silica gel is placed directly in lids suited to the different sampling box formats, which allows for the rapid drying of the samples without mixing between the sample and the desiccant. These lids can be reused without risk of contamination after heat treatment.

FIGS. 8 to 11 show a tool 1' according to a variant embodiment. This tool 1' is distinguished from the one that is the subject of the first embodiment essentially by the mode of actuation of the punch.

According to this variant execution, the punch 2 is fixed at the bottom end of a rigid cylindrical duct 9 engaged with sliding adjustment in the internal volume of the protective casing 6 so as to be guided therein by sliding along a vertical axis. The internal volume of this duct 9 is interconnected with the channel 21 of the punch 2 and is interconnected with the fluid feed head 7, the latter being borne, outside the protective casing 6, by the duct 9.

According to this embodiment, the cannula 8 is also engaged in the internal volume of the duct 9 to be coupled in a seal-tight manner to the feed head 7 in the manner described previously. The duct 9 is fixedly engaged in the first boring 70 of the feed head 7 and its internal volume is interconnected with the end fitting 72 via the first radial boring 71.

A return spring 16 with non-contiguous turns is engaged around the top part of the duct 9. This return spring 16 is compression-mounted between the feed head 7 and a shoulder 62 formed in the casing 6. The purpose of this return spring 16 is to stress the punch 2 toward its first position by acting on the feed head 7. Additionally, the casing 6 is equipped with a gripping handle 63. To maneuver the punch 2 from its initial position to its final position, the operator, while holding the tool 1' in his or her hand by the gripping handle 63, acts on the feed head 7 in the direction of compression of the return spring 16. As will be understood, the rigid duct 9 ensures the transmission of movement and of force between the punch 2 and the feed head 7.

In a preferred embodiment, the duct 9, in the bottom part, comprises an end-fitting form 90. This end-fitting form 90 is coupled to the body of the duct by an annular shoulder 91. A second return spring 17 with non-contiguous turns is engaged around the end-fitting form 90. This return spring 17 bears by its bottom end against the base 60. In the initial position of the punch 2, the shoulder 91 is separated from the top end of the return spring 17 whereas, in the intermediate position of the punch 2, the shoulder 91 is in contact with the top end of the return spring 17 which then exerts an additional resisting force on the duct 9. In this way, a point of resistance, embodying the intermediate position of the punch 2, is formed. The operator, by simple touch sensation, can then assess the position of the punch 2.

It will be understood that the duct 9, the feed head 7, the elastic members 16 and 17, the handle 63 and/or the casing 6 constitute means for actuating the punch between its different positions.

The mode of operation of the tool 1' according to the variant execution is as follows. The operator grasps the tool 1' and moves it toward the plant and engages the opening 4 around one of the leaves of this plant. He or she then actuates the punch 2 toward the die by acting by pushing on the feed head 7 in order to cut a sample from the leaf. The operator then manually keeps the punch 2 in the intermediate position and displaces the tool 1' toward the container provided to receive the sample. The operator acts once again on the punch 2 to bring the latter to the final position and acts on an external control or on a control incorporated in the tool 1' to activate the solenoid valve associated with the appropriate fluid circuit in order to eject the sample.

Figure 12:
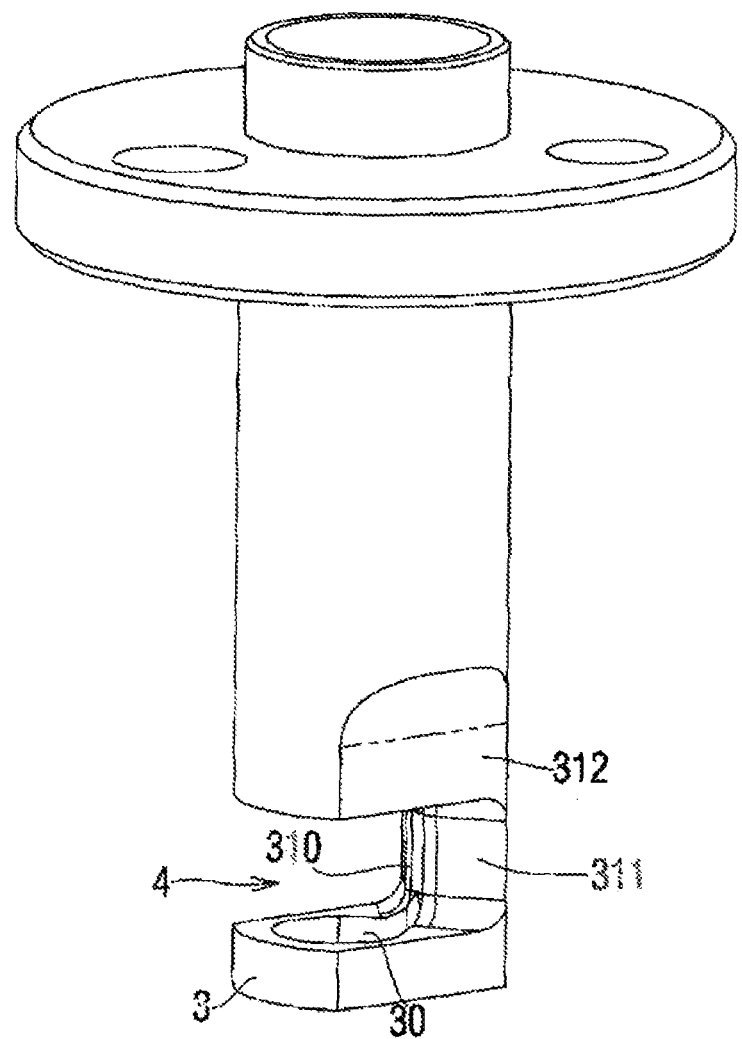
FIG. 12 is a detail view in perspective of a variant execution of the tool and more particularly of its bottom part.
Figure 27:
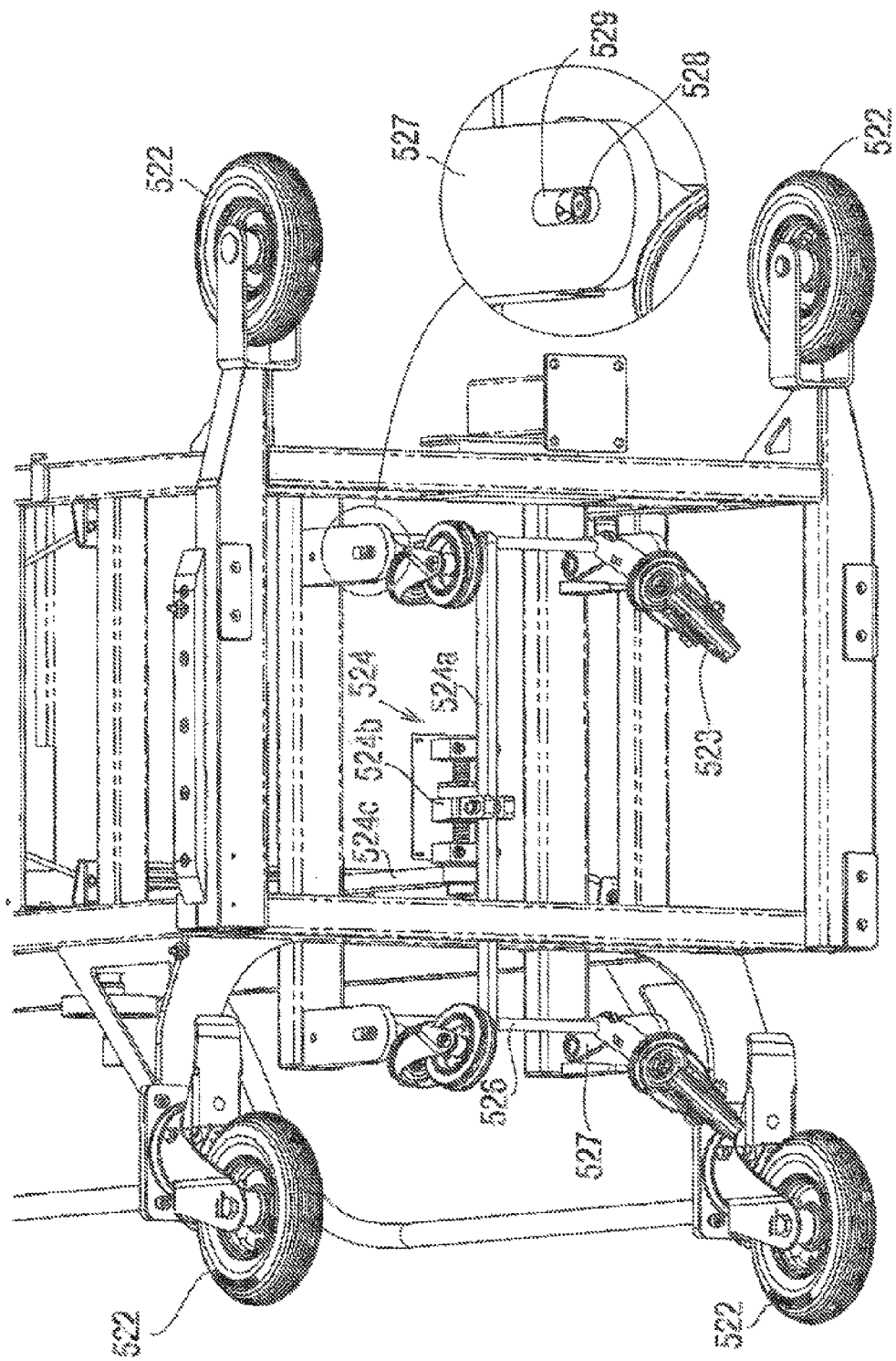
FIG. 27 is a partial view, in perspective from below, of the bottom part of the transport carriage.
Figure 31:
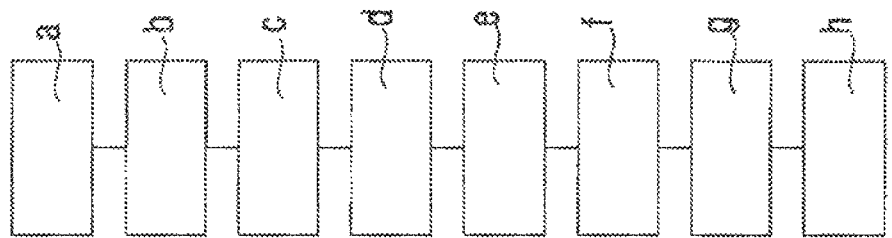
FIG. 31 illustrates the steps of the method, according to the invention, for selectively eliminating plants.
Figure 30:
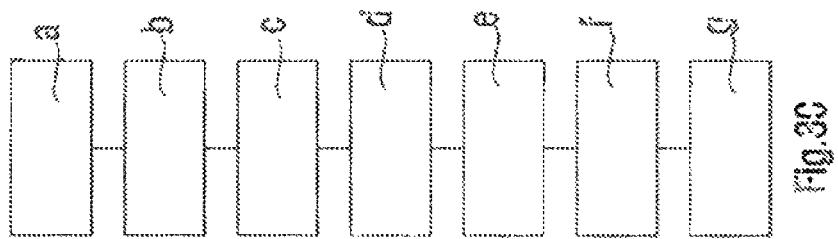
FIG. 30 illustrates the steps of the method, according to the invention, for analyzing the samples.
Figure 29:
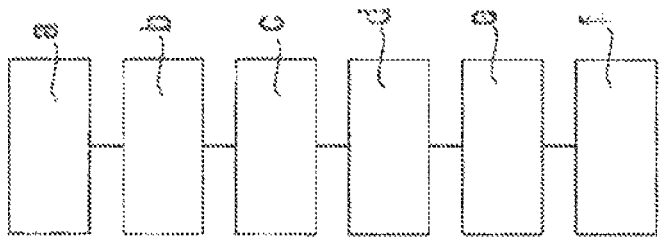
FIG. 29 illustrates the steps of the method, according to the invention, for taking a sample.

FIG. 12 shows a variant execution of the tool 1' according to the invention. It can be seen in these figures that the face 310, over its height (the height corresponding here to the distance between the two top and bottom faces of the opening 4) has two lateral clearances 311, oriented toward the rear. Such an arrangement is a guarantee of being able to apply the perimeter of the leaf to be sampled always against the face 310 and to do so regardless of its contour. Such an arrangement reduces the risk of a leaf to be sampled failing to bear against the face 310 which could lead to the formation of a sample of insufficient size to be able to be used. Furthermore, the guiding body, the wall 31 and the die 3 comprise two opposing flats 312 to facilitate the introduction of the tool into the foliage of the plants to be sampled.

Figure 28:
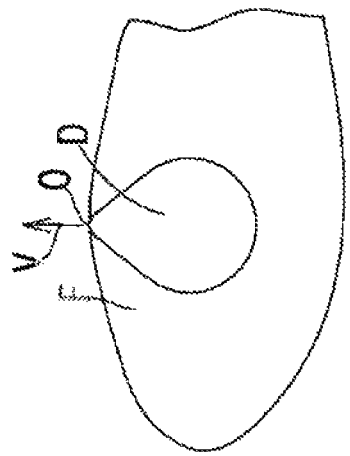
FIG. 28 shows the cut produced in a seedling, for example in one of the leaves thereof.

As can be seen in FIG. 28, the tool as described makes it possible to produce, in the leaf F of a seedling, a cut tangential to the contour of the leaf. Thus, the contour of the cut D has an opening O allowing for the removal of the tool in the direction of the arrow V without damaging the seedling.

The tool 1' according to the invention can equip an automated cell 500 for taking samples. This cell will be able to consist of an enclosure enclosing an automatic machine 510 provided with a manipulating arm 511, preferably multi-axial, bearing the sampling tool 1'. With this cell, according to an exemplary embodiment, there is associated a means 520 for transporting cellular trays 530. This means is suitable for ensuring the transportation of the cellular trays 530 from a plant storage and/or growth area, to the sampling cell and from this sampling cell to the storage and/or growth area, and do so, preferably, in a closed circuit. The storage and/or growth area will be able to consist of a greenhouse or any other type of suitable building. These cellular trays 530, of rectangular form, comprise cells organized according to a regular grid, each receiving a plant in a clod of earth to be sampled. The bottom wall of each cell has a central through perforation for reasons which will become apparent later.

In the preferred embodiment, the transport means 520 consist of a transport carriage provided with horizontal shelves 521 evenly spaced apart vertically, each receiving a cellular tray 530.

The cell will also be able to be equipped with a support table 550, for example that can be displaced height-wise facing the transport carriage 520, and a system 560 for transferring the cellular trays 530 between the carriage 520 and the table 550, and vice versa. This cell will further be able to be equipped with means for supplying sampling boxes 506, these boxes bearing longiform containers or wells, designed to receive the samples collected by the sampling tool 1' from the plants or seedlings. Finally, the cell will be able to be equipped with at least one optical system such as a display system, making it possible, among other things, to check the presence of samples in the containers after each sampling sequence.

FIGS. 13 to 27 show an automated cell according to the invention.

It can be seen in these figures that the enclosure of the cell 500 comprises vertical walls forming a protective jacket around the table, the manipulating arm 511 of the automatic machine 510 and the different conveying elements. Thus, this jacket comprises a vertical rear wall, two lateral walls and a front wall provided with a wide opening in which the cellular tray transport carriage is engaged.

Facing this front wall there is a control cabinet provided with a microcontroller, architectured around a microprocessor and comprising memory modules receiving suitable software. This microcontroller is notably suitable for controlling and monitoring the equipment of the cell and notably the automatic machine 510, its manipulating arm 511 and the tool 1' borne by this manipulating arm.

One of the lateral walls of this enclosure is equipped with an access door. This access door will be associated with an opening detector that is known per se, connected electrically to the microcontroller. In this way, a signal representative of the opening of the door will be able to be detected by the microcontroller which, in return, will act on the motors of the automatic machine 510 to order their immediate stoppage. The restarting of the automatic machine 510 will be able to be performed only using a restart command, external to the enclosure, and functionally associated with the microcontroller. A human presence detector, connected electrically to the microcontroller, will also be positioned in the enclosure to prevent any movement of the manipulating arm 511 of the automatic machine 510 and of the other equipment of the cell should human presence be detected. Similarly, within the volume of the enclosure, there will be able to be a cable actuator. The cable of the actuator will extend horizontally in the enclosure and will be able to be fixed by one of its ends to an elastic member fixed to one of the lateral walls. This cable will be engaged freely in holding rings fixed to the lateral wall and to the rear wall. By its other end, the cable will be fixed to the moving element of the sensor.

The cell comprises a support frame 501 to which the support table 550, the various supply and evacuation conveyors and the optical system or systems are notably fixed.

According to a preferred embodiment, the frame 501 is formed by a number of tubular uprights joined to one another by bracing tubular cross-members.

The support table 550 is fixed to this frame, this table being positioned facing the front opening of the enclosure so as to be positioned facing the transport carriage 520. The area of the table situated facing this opening is called front area. The rear area of the table 550 is situated facing the automatic machine 510, the latter being installed on a suitable support, behind the support table 550.

The support table 550 comprises a top horizontal deck 551 provided to receive the trays 530 bearing the plants in clods of earth, this top deck 551 being borne by a stand 552 formed by four vertical uprights correctly braced by horizontal cross-members.

The top deck 551 of the table comprises through perforations 553 organized in a grid preferably identical to that according to which the through perforations of the cellular tray 530 are organized.

The support table 550 also comprises means for positioning and holding a cellular tray 530 on the top deck 551. According to a preferred embodiment, these means consist of abutments 554 in the form of rollers, installed on the top deck 551. These abutments 554 are designed to bearingly receive the rear edge and one of the lateral edges of the cellular tray 530. These abutments determine a fixed positioning V. Additionally, the holding and positioning means comprise a movable jaw 555 determining a movable positioning V arranged diagonally opposite relative to the first fixed positioning V. This jaw 555 is actuated by a motor member, for example a pneumatic cylinder, to come to act by thrust against one of the corners of the cellular tray 530. The force exerted by the jaw 555 on the corner concerned of the cellular tray 530 is directed diagonally toward the opposite corner. In this way, the tray 530 is pressed firmly against the lateral and rear abutments 554. Furthermore, the support table 550 comprises means for firmly pressing the cellular tray against the deck of the table. These means consist of a horizontal jaw actuated by a motor member coming to act by downward thrust on the horizontal top edge of the support tray. These holding and positioning means thus ensure the temporary immobilization of the cellular tray 530 on the table and the alignment of the through perforations thereof with the through perforations 533 of the top deck 551 of the table 550.

In the volume defined by the stand 552, under the top deck 551, and in the alignment of the through perforations 553 of said top deck, the table 550 comprises lifting vertical rigid rods 556 designed to be engaged, by upward movement, in the through holes of the cellular tray and in the through holes 553 of the top deck 551 to lift the clods of earth and separate them from the corresponding cell. These rigid rods 556 are borne in groups by horizontal plates 557 that can move height-wise and are actuated by motor members. Each vertical rod 556 bears, at its end, a number of gripping needles 558 designed to be inserted into the clod of earth to be raised. In this way, the raised clod of earth is firmly held by these needles 558. Each plate 557 bears only a determined number of rigid rods in order to raise only one clod of earth out of two or one clod of earth out of three or even one clod of earth out of four. Thus, the foliage of the raised plants is separated from the foliage of the adjacent plants. In this way, the risks of taking a sample from an adjacent plant, present when their leaves or their cotyledons are superposed, are reduced.

The horizontal plates 557 are provided with plain bearings by which they are engaged slidingly on common vertical guiding columns, fixed to the stand of the table 552.

The motor members for actuating the plates and rods that they bear consist of pneumatic cylinders fixed by their body to the stand of the table and by their rod to the corresponding plate 557.

Alternatively, according to another embodiment as represented in FIG. 22, each vertical rigid rod 556 is actuated individually, that is to say independently of the other rods 556, by a motor member 556a specific to it. Preferably, this motor member 556a consists of a pneumatic cylinder fed with compressed air by a compressed air source installed under the top deck 551 of the table between the elements of the stand 552. The pneumatic cylinder 556a is supplied with pneumatic energy by a distributor, known per se, driven electrically by the microcontroller.

The system 560 for transferring the cellular trays 530 is suitable for grasping the cellular tray on one of the shelves 521 of the carriage 562 to bring it onto the top deck 551 of the table 550 and, conversely, after the samples have been taken, for bringing the cellular tray 530 onto the shelf 561 of the carriage 562.

According to one embodiment, the transfer system 560 consists of suckers 561 connected to one and the same horizontal boom 562 connected to a vacuum source. This boom is mounted slidingly on at least one horizontal rail, occupying a lateral position on the top deck 551 of the table 550 and extending from the front area to the rear area of this table. The boom 562 is at right angles to the rail and is displaced along this rail by a motor member 563, known per se, consisting of a rodless cylinder. The boom 562, unlike the rail, is borne by a skid formed by a block of tetrafluoroethylene.

According to one embodiment, the table 550 can be moved height-wise in order to bring its top deck 551 level with each shelf 521 of the carriage 520 in order to charge or deposit a cellular tray 530.

To this end, the stand 552 of the table 550 has two diagonally opposite lifting arms 559 fixed to it, and the frame 501 of the cell 500 is provided with two vertical guiding rails 502 each incorporating a motor member for actuating a lifting foot 503. This lifting foot 503 cooperates slidingly with the guiding rail 502. The two lifting arms 559 are respectively borne by the two lifting feet 503 and are secured respectively to these two lifting feet 503 via a floating mount, allowing a vertical sliding movement of the lifting arm 559 relative to the foot 503 which bears it. Through this arrangement, when the stand 552 of the table 550 reaches the floor, the feet 503 can continue their downward travel along the rail 502. Thus, the table 550, in the lowered position, will be able to be placed by its stand on a fixed reference plane of the frame of the sampling cell. This reference plane will advantageously be able to be formed by two bearing sole plates 501a installed fixedly on the floor. In its lowered position bearing on the sole plates 501a, it is necessary for the table 550 to be centered relative to this plane. To this end, each sole plate 501a has positioning bushes each provided with an upwardly open tapered bore and the stand 552 of the support table 500, facing the bushes, has positioning pins of tapered form. Each pin is designed to be engaged, in the lowered position of the table 500, in the bore of the corresponding bush.

Advantageously, each lifting foot 502 comprises a vertical wing mounted slidingly in the vertical guiding rail 502 and fixed to the motor member incorporated therein and a bottom horizontal wing on which the corresponding lifting arm 559 bears when the table 550 is raised. The floating mount is formed by a vertical guiding rail 504, fixed rigidly to the lifting foot and by a slide 505 engaged slidingly on the guiding rail 504 and fixed to the lifting arm 559. The guiding rail 504 and the slide 505 cooperate with one another by guiding grooves and dovetail tenon forms.

The cell 500 comprises means for supplying sampling boxes 506. These means consist of a magazine 505 of sampling boxes 506. This magazine, for example in column form, receives a vertical stack of sampling boxes 506. This magazine is provided, in the bottom part, with a delivery opening through which the bottom box of the stack can be delivered. With this magazine 505 there are associated bottom retention elements, actuated between a position of release and a position of retention by motor members consisting of pneumatic cylinders. Additionally, the magazine has associated with it two other retention elements actuated by motor members to retain the stack of boxes when the last box 506 is dispensed.

The magazine 505 is positioned above the trajectory of a transport pod 507 borne by a rodless cylinder 507b extending from the magazine 505 to an area for parking and collecting samples taken by the tool 1'. This pod 507 is provided with a hollow imprint 507a designed to receive the sampling box 506. Such an imprint arrangement ensures that the sampling box 506 is held on the pod 507 when transported from the magazine 505 to the sample parking and collection area. Preferably, the rodless cylinder 507b occupies a lateral position relative to the support table 550.

The sample parking and collection area is provided with means for positioning and holding the sampling box 506, these means consisting of a first V-shaped fixed jaw 508 fixedly installed on said parking area and a second V-shaped movable jaw 509. These jaws both act with thrust on two diagonally opposite corners of the sampling box 506. The movable jaw 509 is actuated by a motor member such as a pneumatic cylinder.

Thus, the sampling box 506 is perfectly maintained in a position suitable for receiving the samples taken from the seedlings by the sampling tool 1'. In order to deposit the sample taken into the corresponding container, the tool 1' is made to penetrate by a few millimeters into the container.

Adjoining the parking area and the actuation cylinder 507b for the transport pod 507 for the sampling boxes 506, there is a conveyor 500b, for evacuating said boxes 506 to a reception area. This conveyor 500b is arranged with a slight slope to evacuate the boxes of samples to the reception area.

Between the parking area and the evacuation conveyor 500b, there is a transfer means 540 suitable first of all for grasping the sampling box 506 present in the parking area and then for transferring this box 506 to the evacuation conveyor 500b.

According to one embodiment, this transfer means 540 comprises suckers 541 borne by a housing 542, the internal chamber of which is interconnected on the one hand with a vacuum source and on the other hand with the suckers. The transfer means 540 further comprises an actuating motor 543, for example a pneumatic cylinder, to which the housing 542 is fixed.

Advantageously, the bottom wall of the transport pod 507, the wall on which the sampling box 506 rests, is transparent to light and the sampling box 506 and the containers or wells that it bears are also transparent to light. Additionally, the pod 507 incorporates a back-lighting source suitable for lighting the sampling box from below. Also, above the sample parking and collection area, vertical to said area, there is a telecentric vision system 570, by which the correct filling of the containers or wells of the sampling box 506 positioned on the parking area with samples can be observed. This vision system 570 is connected to the microcontroller of the cell.

The cell 500 further comprises a mount 580 bearing two optical systems oriented toward the support table. This mount 580 and the systems that it bears can be displaced horizontally above and at a distance from the table 550, for example in a direction at right angles to the direction of displacement of the cellular tray 530 on the top deck 551 of the table 550. One of the optical systems consists of a first viewing camera 581. The optical axis of this camera is vertical. The other optical system consists of a stereoscopic camera or 3D camera, 582, and a laser ray source 583. The optical axis of the stereoscopic camera is inclined relative to the vertical whereas the optical axis of the laser source is vertical. The camera 581 or 2D camera makes it possible to check the viability of the seedling, whereas the camera 582, in association with the laser ray source 583, makes it possible to obtain a three-dimensional representation of the seedlings via the deformation of the laser line. For the purpose of this checking and obtaining of images, the mount 580 is displaced over the cellular tray 530, the latter and the seedlings that it bears all being lit by the laser ray.

The mount 580 is borne by a carriage 584 mounted on top horizontal guiding rails fixed to the frame 501 of the cell 500. This carriage 584 can be displaced along these rails by a motor assembly 585 comprising an electric motor 585*a* with rotary output shaft and a movement transmission with notched pinions 586, 587 and notched belt 588. One of the two pinions, the driving pinion 586, is fixed to the output shaft of the electric motor 586*a* whereas the other, the driven pinion 587, is fixed to an axis engaged in bearings borne by a clevis fixed to the frame 501 of the cell 500. The notched belt 588 is fixed to the carriage 584. The axis of the driving pinion 587, beyond one of its bearings, is coupled to a coder 589 that is known per se, electrically connected to the microcontroller. This arrangement makes it possible to determine the position of the mount 580 along the rails.

Advantageously, the cell 500 has an associated tank, not represented, provided to contain a solution for washing the sampling tool 1'. Thus, after a determined number of samples have been taken, the sampling tool 1' will be dipped by the automatic machine 510 in this washing solution. The periodic washing of the tool 1' makes it possible to reduce the risk of the sample taken remaining stuck in the die 3 of this tool 1'. This washing container will be able to be borne by the support table 550.

The microcontroller has connected to it, via suitable interfaces, the various electrical equipment items of the cell 500, these electrical equipment items being, in a nonlimiting manner, the automatic machine 510 and its various motors, the electric drivers of the various pneumatic cylinders, the motor of each rail 502, the motor 585*a* for displacing the mount 580, the various end-of-travel sensors associated with the moving elements of the cell and the various presence detectors. The microcontroller also has the various optical systems connected to it for the purpose of image analysis.

This cell 500 will advantageously be equipped with identifier readers that are known per se. These identifiers will be borne by the cellular trays 530 and by the sampling boxes 506. These identifiers will be able to consist of labels bearing barcodes, RFID chips, or any other identifier. The cellular tray identification reader will advantageously be borne by the support table 550. This way, the identification code of the tray 530 will be able to be read before transfer to the support table 550 and an error message will then be able to be generated by the microcontroller in the case of a nonconforming cellular tray 530. These identifier readers will be connected to the microcontroller. By these means and using suitable software, it will now be possible to ensure that the samples taken can be traced. To facilitate this tracing, the distribution of the wells or containers of each sampling box 506 will reproduce, on a smaller scale, the distribution of the cells of each cellular tray 530 and the sampling boxes 506, at least in the sample parking and collection area, will be positioned in such a way that the rows and columns formed by the distribution of the wells or containers are respectively parallel to the rows and columns formed by the distribution of the cells of the cellular tray 530. Such arrangements establish a relationship between the position of each cell and the position of each well or container in order for the taking of a sample from one of the cells to be reflected in the deposition of this sample into the counterpart container. Thus, the continuous monitoring applied via the telecentric vision system 570 will make it possible to detect not only the lack of samples in the wells, but also to detect a deposition in a well already filled, or a deposition in a well not intended to receive the sample concerned, or even, a correct deposition in the well that is the counterpart of the cell from which the sample was taken. If a nonconforming deposition is detected, the microcontroller will be able to generate an error signal and to stop any taking of samples.

The identification of the cellular trays 530 and of the sampling boxes 506 makes it possible to establish an association between a tray 530 and a box 506. Thus, the reading of the identifier of the sampling box 506, present on the sample parking and collection area, will initiate the search for the corresponding tray 530 by the microcontroller. This search will be carried out by upward displacement of the support table 550 facing the carriage 520 and by reading the identifier of the tray borne by each shelf 521.

The reading of the identifier, or a specific marker, notably with regard to the sampling box 506, makes it possible to ensure that it is positioned correctly. It is not however, desirable to stop the sampling if this box 506 is incorrectly positioned. For this reason, the microcontroller and its matching software will be able to take account of this incorrect positioning for the purpose of a conforming distribution of samples in the wells of the sampling box.

The automated cell 500 will be able to receive a means 600 for eliminating plants in clods of earth by suction. This means will be able to consist of a suction plant 601 comprising a suction mouth interconnected with a suction duct 602 bearing, at a distance from the plant, a suction end-fitting 603. This suction end-fitting 603 will be able to be engaged removably in a collar 604 borne by the manipulating arm 511, or, as represented in the attached figures, by the sampling tool 1'.

Such a means will be used to destroy the plants not selected after their DNA or their RNA has been analyzed. For this destruction, the data relating to the discarded plants and to the cellular trays which bear them will be transmitted by any suitable means to the microcontroller, and the cellular trays 530 concerned will be once again loaded onto the transport means 520 to be transported to the automated cell 500 to be then transferred by the transfer system 560 to the support table 550 in order for the plants or seedlings that have not been retained to be removed from the corresponding cells of the cellular tray 530, by suction. To this end, the manipulating arm 511 will position the suction end-fitting 603 in line with the seedling to be eliminated and the suction will be activated in order for the seedling to be extracted from the corresponding cell of the tray 530.

The front opening of the enclosure of the cell 500 is associated with two guiding elements forming a V for positioning the transport carriage 520 for the cellular trays 530. These guiding elements are fixed to the floor and have, above the floor, two horizontal bearing flanges 500a, provided to bearingly receive two lateral bearing elements 520a of the carriage 520.

This transport carriage 520 consists of a frame bearing, at regular intervals, the support shelves 521 for the cellular trays 530. This frame is equipped with two lateral bearing elements 520a, in the form of arms, provided to come to bear on the two horizontal flanges 500a associated with the front opening of the enclosure.

Advantageously, the carriage has two sets of rolling members 522, 523, of which one can be used for displacement outside and the other for displacement inside and notably around the outside of the cell. In this way, the risks of pollution of the samples by external agents is reduced.

One of the two sets of rolling members 522 is fixed directly to the frame of the carriage 520 whereas the other 523 is borne by a raising and lowering system 524, secured to the frame and actuated for example by a crank 525. By the actuation of the raising and lowering system, the rolling members 523 are brought to bear on the floor in order to separate the rolling members 522 from the floor by lifting the carriage 520. In this position, the bearing elements 520a, are situated at a higher level relative to the two flanges 500a and the carriage 520 can be freely introduced between the two guiding elements. An abutment fixed to the floor limits the travel of the carriage 520 to the support table 550. After the introduction of the carriage 520, the raising and lowering system is once again actuated in the direction of lowering of the carriage 520 in order for the two lateral bearing elements 520a to be able to come to bear on the two bearing flanges 500a. Thus, the carriage 520 is immobilized facing the support table 550, under the effect of its own weight.

The raising and lowering system comprises two axles 526 on each of which two rolling members 523 are installed, these axles being borne by fixing each at the end of two articulated connecting rods 527 to the frame of the carriage 520. Each rolling member 523 has an axis by which it is fixed to the corresponding axle. This axis comprises a pin 528 engaged in a slide 529 formed in a tab of the frame of the carriage. These axles are secured to a common maneuvering arm 524a fixed to the nut of a screw and nut mechanism 524b of which the screw is maneuvered by the crank 525 via a movement transmission with notched pinions and notched belt 524c. One of the pinions is engaged with the crank 525, the other pinion is engaged with the screw of the screw and nut mechanism 524b. The belt 524c is mounted on the two notched pinions.

Alternatively, the means for transporting the cellular trays 530 between the plant storage and/or growth area and the automated cell for taking samples 500, and, conversely, between this cell 500 and said area, consists of a conveyor, for example, with motorized rollers, said conveyor being provided to allow the displacement of the cellular trays 530 from said storage area to the cell 500, followed by their return to their storage area once the sampling has been done, for example in a closed circuit. It is obvious that any other type of conveyor, for example with endless belt, with rollers, with chain or with track wheels, will be able to be used to transport the cellular trays 530.

Similarly, any transport means other than the carriage as described and a conveyor will be able to be used.

It goes without saying that the present invention can receive all arrangements and variants in the field of the technical equivalents without in any way departing from the framework of the present patent as defined by the claims hereinbelow.

The invention claimed is:

1. A sampling tool for sampling plant tissues, comprising:
a guiding body provided with a first through bore;
a part-holding punch mounted with a sliding adjustment in the first through bore, the part-holding punch comprising a bottom edge of a closed contour forming a cutting edge;
a part-holding die, secured to the guiding body, positioned under the guiding body and separated from the guiding body by an introduction opening for a plant to be cut, the part-holding die being provided, in an axial alignment of the first through bore, with a second through bore into which a bottom end of the punch penetrates for cutting a sample to be taken from the plant, the introduction opening being limited by a bottom face corresponding to a top face of the part-holding die, a top face corresponding a bottom face of the guiding body and a rear vertical face of a wall linking the part-holding die to the guiding body, the second through bore being provided with a top edge of a closed contour forming a cutting edge;
an actuator to actuate the part-holding punch between an initial position where the part-holding punch is retracted into the guiding body, a stable intermediate position of a temporary stoppage where the bottom edge of the part-holding punch is situated in the second through bore, and a final position where the part-holding punch passes right through the part-holding die and the bottom edge of the part-holding punch is outside the second through bore; and
wherein a contour of each rear part of cross section of the bottom end of the part-holding punch and cross section of the second through bore is tangential to a vertical geometrical plane containing the rear vertical face of the introduction opening.

2. The sampling tool as claimed in claim 1, wherein a trajectory of the part-holding punch is tangential to the rear vertical face of the introduction opening; and wherein the second through bore is tangential to a geometrical plane containing the rear vertical face to produce, in the plant from which the sample is to be taken, a cut with an open contour.

3. The sampling tool as claimed in claim 2, wherein each of the cross section of the bottom end of the part-holding punch and the cross section of the second through bore has a front part and a rear part, the front part being wider than the rear part.

4. The sampling tool as claimed in claim 1, wherein the part-holding punch further comprises, at its bottom end, an ejector to eject at least one of a gaseous fluid and a liquid fluid.

5. The sampling tool as claimed in claim 4, wherein the ejector comprises a gaseous or liquid fluid feed head; an internal channel to dispense said at least one of the gaseous and the liquid fluid, the internal channel formed in the part-holding punch and interconnected with the gaseous or liquid fluid feed head; and at least one nozzle formed at the bottom end of the part-holding punch and emerging in a bottom face thereof, said at least one nozzle being interconnected with the internal channel of the part-holding punch.

6. The sampling tool as claimed in claim 5, wherein the internal channel receives a cannula to dispense said at least one of gaseous and liquid fluid, interconnected on one end to the gaseous or liquid fluid feed head and on other end to said at least one nozzle.

7. The sampling tool as claimed in claim 6, wherein a diameter of the cannula is smaller than a diameter of the internal channel to form a pathway for said at least one of gaseous and liquid fluid between the cannula and the internal channel, the pathway being interconnected on one end to the gaseous or liquid feed head and on other end to said at least one nozzle.

8. The sampling tool as claimed in claim 1, wherein the actuator is a motor comprising an output element with a linear displacement.

9. The sampling tool as claimed in claim 5, further comprising a protective casing with a bottom base to which the guiding body is fixed; a rigid cylindrical duct to which the part-holding punch is fixed to its bottom end, the rigid cylindrical duct engaged with a sliding adjustment in an internal volume of the protective casing so as to be guided therein by a sliding movement along a vertical axis, an internal volume of the rigid cylindrical duct is interconnected with the internal channel and the gaseous or liquid fluid feed head being borne externally to the protective casing by the rigid cylindrical duct.

10. An automatic machine for taking samples comprising a manipulating arm bearing bearing the sampling tool as claimed in claim 1.

11. An automated cell for taking samples, comprising:
   a support table to receive cellular trays bearing plants in clods of earth to be sampled;
   an automatic machine provided with a manipulating arm; and
   a sampling tool as claimed in claim 1 borne by the manipulating arm of the automatic machine.

12. The automated cell as claimed in claim 11, wherein the support table comprises a transfer system for the cellular trays, configured to ensure transfer of the cellular trays between the support table and a transport device to transport the cellular trays.

13. The automated cell as claimed in claim 12, wherein the support table comprises a stand on which is installed a top horizontal deck provided to receive each cellular tray from the transport device, and a positioning device to position and hold a cellular tray on the top horizontal deck.

14. The automated cell as claimed in claim 13, wherein the top horizontal deck comprises through perforations organized according to a grid corresponding to an organization of through perforations of the cellular tray; and wherein the support table, under the top horizontal deck and in an alignment of the through perforations of the top horizontal deck, comprises lifting vertical rigid rods configured to engage, by an upward movement, into the through perforations of the top horizontal deck and the through perforations of the cellular tray to lift the clods of earth and separate them from a corresponding cell.

15. The automated cell as claimed in claim 13, further comprising two diagonally opposite lifting arms fixed to the stand of the support table; wherein a frame of the automated cell is provided with two vertical guiding rails, each vertical guiding rail incorporating a motor member to actuate a lifting foot cooperating slidingly with said each guiding rail; and wherein the two diagonally opposite lifting arms being respectively borne by the two lifting feet and being secured respectively to the two lifting feet via a floating mount allowing a sliding vertical movement of a respective lifting arm relative to the lifting foot bearing the respective lifting arm.

16. The automated cell as claimed in claim 13, further comprising a parking area to park sampling boxes and to collect samples, the parking area being equipped with a device to position and hold a sampling box.

17. The automated cell as claimed in claim 16, wherein the sampling box is born by a transport pod configured to move between a magazine and the parking area, the transport pod is provided with a hollow imprint to receive the sampling box, a bottom wall of the transport pod is transparent to light, the transport pod comprises a backlighting source configured to light the sampling box from below; and further comprising a telecentric vision system positioned above and vertical to the parking area, to observe filling of containers or wells borne by the sampling box with samples.

18. The automated cell as claimed in claim 11, further comprising a mount bearing first and second optical systems oriented toward the support table, the mount and the first and second optical systems are configured to be displaced horizontally above and at a distance from the support table; wherein the first optical system comprises a first camera; and wherein the second optical system comprises a stereoscopic camera and a laser ray source.

19. A method for taking a sample, comprising the steps of:
   moving a sampling tool toward a previously selected plant or alternatively moving the previously selected plant toward the sampling tool comprising:
      a guiding body provided with a first through bore;
      a part-holding punch mounted with a sliding adjustment in the first through bore, the part-holding punch comprising a bottom edge of a closed contour forming a cutting edge;
      a part-holding die, secured to the guiding body, positioned under the guiding body and separated from the guiding body by an introduction opening for a plant to be cut, the part-holding die being provided, in an axial alignment of the first through bore, with a second through bore into which a bottom end of the punch penetrates for cutting a sample to be taken from the plant, the introduction opening being limited by a bottom face corresponding to a top face of the part-holding die, a top face corresponding a bottom face of the guiding body and a rear vertical face of a wall linking the part-holding die to the guiding body, the second through bore being provided with a top edge of a closed contour forming a cutting edge;
      an actuator to actuate the part-holding punch between an initial position where the part-holding punch is retracted into the guiding body, a stable intermediate position of a temporary stoppage where the bottom edge of the part-holding punch is situated in the second through bore, and a final position where the part-holding punch passes right through the part-holding die and the bottom edge of the part-holding punch is outside the second through bore; and
      wherein a contour of each rear part of cross section of the bottom end of the part-holding punch and cross section of the second through bore is tangential to a vertical geometrical plane containing the rear vertical face of the introduction opening;
   engaging the introduction opening on either side of one of leaves of the previously selected plant;
   cutting the sample by punching a leaf of the previously selected plant by moving the part-holding punch from the initial position to the stable intermediate position;
   keeping the part-holding punch in the stable intermediate position to keep the sample in the second through bore;
   removing the sampling tool or alternatively the previously selected plant while maintaining the part-holding punch in the stable intermediate position; and
   depositing the sample in a dedicated container.

20. A method for analyzing samples, comprising the steps of taking the samples as claimed in claim 19; and analyzing DNA of the samples.

\* \* \* \* \*